(12) United States Patent
Gil et al.

(10) Patent No.: US 12,115,264 B2
(45) Date of Patent: *Oct. 15, 2024

(54) STERILIZATION AND FILTRATION OF PEPTIDE COMPOSITIONS

(71) Applicant: 3-D Matrix, Ltd., Tokyo (JP)

(72) Inventors: Eun Seok Gil, Acton, MA (US); Karl Patrick Gilbert, Danvers, MA (US)

(73) Assignee: 3-D Matrix, Ltd., Tokyo (JP)

(*) Notice: Subject to any disclaimer, the term of this patent is extended or adjusted under 35 U.S.C. 154(b) by 300 days.

This patent is subject to a terminal disclaimer.

(21) Appl. No.: 17/372,424

(22) Filed: Jul. 10, 2021

(65) Prior Publication Data

US 2022/0001047 A1    Jan. 6, 2022

Related U.S. Application Data

(60) Continuation of application No. 16/171,734, filed on Oct. 26, 2018, now Pat. No. 11,090,398, which is a division of application No. 15/122,749, filed as application No. PCT/IB2015/000868 on Mar. 10, 2015, now Pat. No. 10,369,237.

(60) Provisional application No. 61/950,536, filed on Mar. 10, 2014.

(51) Int. Cl.
| | | |
|---|---|---|
| A61L 2/02 | (2006.01) | |
| A61L 2/04 | (2006.01) | |
| A61L 2/07 | (2006.01) | |
| C07K 7/08 | (2006.01) | |

(52) U.S. Cl.
CPC ............... *A61L 2/022* (2013.01); *A61L 2/04* (2013.01); *A61L 2/07* (2013.01); *C07K 7/08* (2013.01); *A61L 2202/21* (2013.01)

(58) Field of Classification Search
CPC ... A61L 2/022; A61L 2/04; A61L 2/07; A61L 2202/21; A61L 2/0017; A61L 2/0023; C07K 7/08

See application file for complete search history.

(56) References Cited

U.S. PATENT DOCUMENTS

| | | | |
|---|---|---|---|
| 4,466,641 A | 8/1984 | Heilman et al. | |
| 4,582,640 A | 4/1986 | Smestad et al. | |
| 4,642,117 A | 2/1987 | Nguyen et al. | |
| 4,947,840 A | 8/1990 | Yannas et al. | |
| 5,110,604 A | 5/1992 | Chu et al. | |
| 5,126,141 A | 6/1992 | Henry | |
| 5,236,903 A | 8/1993 | Saiki et al. | |
| 5,292,514 A | 3/1994 | Capecchi et al. | |

(Continued)

FOREIGN PATENT DOCUMENTS

| | | |
|---|---|---|
| CA | 2572964 A1 | 2/2006 |
| CA | 2618184 A1 | 12/2006 |

(Continued)

OTHER PUBLICATIONS

International Preliminary Report on Patentability, PCT/IB2015/00868, 10 pages, Sep. 13, 2016.

(Continued)

*Primary Examiner* — Regina M Yoo
(74) *Attorney, Agent, or Firm* — IP Supra, PLLC; Constantine Linnik; Beth L. Smiley

(57) ABSTRACT

Methods and devices for sterilizing viscous peptide compositions which have shear thinning rheological properties at high concentrations.

8 Claims, 15 Drawing Sheets

Specification includes a Sequence Listing.

(56) References Cited

U.S. PATENT DOCUMENTS

| | | |
|---|---|---|
| 5,510,102 A | 4/1996 | Cochrum |
| 5,527,610 A | 6/1996 | Urry |
| 5,550,187 A | 8/1996 | Rhee et al. |
| 5,670,483 A | 9/1997 | Zhang et al. |
| 5,747,452 A | 5/1998 | Rusiahti et al. |
| 5,773,577 A | 6/1998 | Cappello |
| 5,955,343 A | 9/1999 | Holmes et al. |
| 6,046,160 A | 4/2000 | Obi-Tabot |
| 6,224,893 B1 | 5/2001 | Langer et al. |
| 6,280,474 B1 | 8/2001 | Cassidy et al. |
| 6,548,630 B1 | 4/2003 | Zhang et al. |
| 6,730,298 B2 | 5/2004 | Griffith-Cima et al. |
| 6,800,481 B1 | 10/2004 | Holmes et al. |
| 7,098,028 B2 | 8/2006 | Holmes et al. |
| 7,449,180 B2 | 11/2008 | Kisiday et al. |
| 7,598,343 B1 | 10/2009 | Krishna et al. |
| 7,713,923 B2 | 5/2010 | Genove et al. |
| 7,846,891 B2 | 12/2010 | Ellis-Behnke et al. |
| 8,022,178 B2 | 9/2011 | Hori et al. |
| 8,901,084 B2 | 12/2014 | Genove et al. |
| 9,012,404 B2 | 4/2015 | Spirio et al. |
| 9,084,837 B2 | 7/2015 | Ellis-Behnke et al. |
| 9,162,005 B2 | 10/2015 | Ellis-Behnke et al. |
| 9,327,010 B2 | 5/2016 | Ellis-Behnke et al. |
| 9,339,476 B2 | 5/2016 | Norchi et al. |
| 9,364,513 B2 | 6/2016 | Ellis-Behnke et al. |
| 9,415,084 B2 | 8/2016 | Ellis-Behnke et al. |
| 9,439,941 B2 | 9/2016 | Ellis-Behnke et al. |
| 9,724,448 B2 | 8/2017 | Kobayashi et al. |
| 10,245,299 B2 | 4/2019 | Mehta et al. |
| 10,369,237 B2 | 8/2019 | Gil et al. |
| 10,612,003 B2 | 4/2020 | Yliperttula et al. |
| 11,090,398 B2 | 8/2021 | Gil et al. |
| 2002/0160471 A1 | 10/2002 | Kisiday et al. |
| 2003/0069177 A1 | 4/2003 | Dubaquie et al. |
| 2003/0166846 A1 | 9/2003 | Rothstein et al. |
| 2004/0204561 A1 | 10/2004 | Ellison |
| 2004/0242469 A1 | 12/2004 | Lee et al. |
| 2005/0181973 A1 | 8/2005 | Genove et al. |
| 2005/0287186 A1 | 12/2005 | Ellis-Behnke et al. |
| 2006/0084607 A1 | 4/2006 | Spirio et al. |
| 2006/0146703 A1 | 7/2006 | Lee et al. |
| 2006/0148703 A1 | 7/2006 | Lee et al. |
| 2006/0293243 A1* | 12/2006 | Puri ............ A61K 9/0019 530/328 |
| 2007/0128175 A1 | 6/2007 | Ozbas et al. |
| 2007/0190603 A1 | 8/2007 | Holmes et al. |
| 2008/0032934 A1 | 2/2008 | Ellis-Behnke et al. |
| 2008/0091233 A1 | 4/2008 | Ellis-Behnke et al. |
| 2008/0091233 A1 | 4/2008 | Ellis-Behnke et al. |
| 2009/0053103 A1 | 2/2009 | Mortimer et al. |
| 2009/0111734 A1 | 4/2009 | Ellis-Behnke et al. |
| 2009/0162437 A1 | 6/2009 | Horii et al. |
| 2009/0169598 A1 | 7/2009 | Crutcher |
| 2009/0269443 A1* | 10/2009 | van Beckhoven ...... A23L 2/52 426/74 |
| 2010/0143504 A1 | 6/2010 | Spirio et al. |
| 2010/0311640 A1 | 12/2010 | Genove et al. |
| 2011/0002860 A1 | 1/2011 | Takamura et al. |
| 2011/0201541 A1 | 8/2011 | Takamura et al. |
| 2012/0010140 A1 | 1/2012 | Ellis-Behnke et al. |
| 2012/0058066 A1* | 3/2012 | Nagai ............ C12N 5/0658 427/256 |
| 2012/0070427 A1 | 3/2012 | Kaplan et al. |
| 2013/0281547 A1 | 10/2013 | Spirio et al. |
| 2013/0298239 A1 | 11/2013 | Takamura et al. |
| 2014/0010790 A1 | 1/2014 | Yliperttula et al. |
| 2014/0038909 A1 | 2/2014 | Takamura et al. |
| 2014/0286868 A1 | 9/2014 | Nagai et al. |
| 2014/0286888 A1* | 9/2014 | Nagai ............ C12N 5/0656 252/194 |
| 2014/0329914 A1 | 11/2014 | Kobayashi et al. |
| 2014/0378549 A1 | 12/2014 | Voigts et al. |
| 2015/0105336 A1 | 4/2015 | Takamura et al. |
| 2015/0197359 A1* | 7/2015 | Nohara ............ C07K 1/36 53/425 |
| 2015/0258166 A1 | 9/2015 | Soirio et al. |
| 2015/0290329 A1 | 10/2015 | Heilshorn et al. |
| 2015/0307835 A1* | 10/2015 | Jeannin ............ A61K 47/42 530/328 |
| 2015/0328279 A1 | 11/2015 | Ellis-Behnke et al. |
| 2016/0000966 A1 | 1/2016 | Kobayashi et al. |
| 2016/0015855 A1 | 1/2016 | Nohara et al. |
| 2016/0030628 A1 | 2/2016 | Kobayashi |
| 2016/0030629 A1 | 2/2016 | Sun et al. |
| 2016/0213906 A1 | 7/2016 | Horita et al. |
| 2016/0287744 A1 | 10/2016 | Kobayashi et al. |
| 2016/0317607 A1 | 11/2016 | Spirio et al. |
| 2016/0362451 A1 | 12/2016 | Gil et al. |
| 2017/0072008 A1 | 3/2017 | Mehta et al. |
| 2017/0128622 A1 | 5/2017 | Spirio et al. |
| 2017/0173221 A1 | 6/2017 | Mehta et al. |
| 2017/0202966 A1 | 7/2017 | Gil et al. |
| 2017/0173105 A1 | 8/2017 | Mehta et al. |
| 2018/0369452 A1 | 12/2018 | Maki et al. |

FOREIGN PATENT DOCUMENTS

| | | |
|---|---|---|
| CN | 101198350 A | 6/2008 |
| CN | 101378773 A | 3/2009 |
| CN | 101514225 A | 8/2009 |
| DE | 3005495 A1 | 8/1981 |
| EP | 2146667 A2 | 1/2010 |
| EP | 2345433 A1 | 7/2011 |
| EP | 2823830 A1 | 1/2015 |
| EP | 3031466 A1 | 6/2016 |
| JP | 2005-515796 A | 6/2005 |
| JP | 2005-263631 A | 9/2005 |
| JP | 2007-105186 A | 4/2007 |
| JP | 2007-524420 A | 8/2007 |
| JP | 2007-526232 A | 9/2007 |
| JP | 2008-505919 A | 2/2008 |
| JP | 2008-539257 A | 11/2008 |
| JP | 2008-546689 A | 12/2008 |
| JP | 2009-011341 A | 1/2009 |
| JP | 2009-535338 A | 10/2009 |
| JP | 2010-280719 A | 12/2010 |
| JP | 2012-082180 A | 4/2012 |
| JP | 5255274 B2 | 8/2013 |
| JP | 2014-527543 A | 10/2014 |
| JP | 5730828 B2 | 6/2015 |
| JP | 5922749 B2 | 5/2016 |
| WO | WO-94/17811 A1 | 8/1994 |
| WO | WO-1996/040033 A1 | 12/1996 |
| WO | WO-1997/037694 A1 | 10/1997 |
| WO | WO-99/53019 A1 | 10/1999 |
| WO | WO-00/01238 A1 | 1/2000 |
| WO | WO-2002/022072 A2 | 3/2002 |
| WO | WO-02/062969 A2 | 8/2002 |
| WO | WO-2002/058749 A2 | 8/2002 |
| WO | WO-2002/062961 A2 | 8/2002 |
| WO | WO-03/084980 A2 | 10/2003 |
| WO | WO-03/096972 A2 | 11/2003 |
| WO | WO-2004/007532 A2 | 1/2004 |
| WO | WO-2005/001076 A2 | 1/2005 |
| WO | WO-2005/014615 A2 | 2/2005 |
| WO | WO-2005/082399 A2 | 9/2005 |
| WO | WO-2006/014570 A2 | 2/2006 |
| WO | WO-2006/116524 A1 | 11/2006 |
| WO | WO-2006/138023 A1 | 12/2006 |
| WO | WO-2007/076032 A2 | 7/2007 |
| WO | WO-2007/142757 A2 | 12/2007 |
| WO | WO-2008/039483 A2 | 4/2008 |
| WO | WO-2008/073392 A2 | 6/2008 |
| WO | WO-2008/073395 A2 | 6/2008 |
| WO | WO-2008/113030 A2 | 9/2008 |
| WO | WO-2008/127607 A2 | 10/2008 |
| WO | WO-2008/134544 A1 | 11/2008 |
| WO | WO-2009/072556 A1 | 6/2009 |
| WO | WO-2010/041636 A1 | 4/2010 |
| WO | WO-2012/008967 A1 | 1/2012 |
| WO | WO-2013/030673 A2 | 3/2013 |
| WO | WO-2013/133413 A1 | 9/2013 |

(56) References Cited

FOREIGN PATENT DOCUMENTS

| | | |
|---|---|---|
| WO | WO-2014/008400 A2 | 1/2014 |
| WO | WO-2014/076660 A1 | 5/2014 |
| WO | WO-2014/136081 A1 | 9/2014 |
| WO | WO-2014/138081 A1 | 9/2014 |
| WO | WO-2014/141143 A1 | 9/2014 |
| WO | WO-2014/141160 A1 | 9/2014 |
| WO | WO-2015/027203 A1 | 2/2015 |
| WO | WO-2015/030063 A1 | 3/2015 |
| WO | WO-2015/136370 A2 | 9/2015 |
| WO | WO-2015/138473 A1 | 9/2015 |
| WO | WO-2015/138475 A1 | 9/2015 |
| WO | WO-2015/138478 A1 | 9/2015 |
| WO | WO-2015/138514 A1 | 9/2015 |
| WO | WO-2017/120092 A1 | 7/2017 |

OTHER PUBLICATIONS

Wang, T. et al. Molecular Mechanisms of RADA16-1 Peptide on Fast Stop Bleeding in Rat Models, Int. J. Mol. Sci., 13: 15279-15290 (2012).

Cai, L. et al, Injectable Hydrogels with In Situ Double Network Formation Enhance Retention of Transplanted Stem Cells, Adv. Funct. Mater., 1-8 (2015).

3-D Matrix Japan, Ltd. Company Profile Power Point, 32 pages, May 2005 (with English translation).

3-D Matrix Japan, Ltd., Products and FAQs, with English Translation, 14 pages. URL: http:/web.archive.org [Retrieved Oct. 21, 2016].

3D Matrix Japan, Company, Technology, Products, Technology, FAQs, Publication, Company, News, Contact, no English translation, 17 pages. URL: http://www.3d-matrix.co.jp/cm02.html [Retrieved Feb. 25, 2005].

3D Matrix Japan, Product Features, with English translation, 2 pages. URL: http://web.archive.org/web/20050416044014/http://www.3d-matrix.eo.jp/pr03.html [Retrieved Feb. 20, 2013].

3D Matrix Japan, Product List, with English translation, 2 pages. URL: http:/web.archive.org/web/20050416043834/http://www.3d-matrix.co.jp/pr02.html [Retrieved Aug. 1, 2013].

3D Matrix Japan, Products, with English translation, 2 pages. URL: http://web.archive.org/web/20050415004502/http://www.3d-matrix.eo.jp/pr0I.html [Retrieved Feb. 20, 2013].

3D-Matrix Japan, Products, FAQs, 8 pages, dispatched Sep. 20, 2011 [English translation].

BD PuraMatrix Peptide Hydrogel, Catalog No. 354250, BD Biosciences, 1-16 (2004).

BD PuraMatrix Peptide Hydrogel, Product Specification Sheet, 1 page.

Declaration of Dr. Terence Norchi, MD, for use in proceedings against EP 1879606, 4 pages (Mar. 31, 2016).

Declaration of Rutledge Ellis-Behnke for WO 2006/116524, 6 pages, Aug. 10, 2015.

Eisenbud, D. et al, Hydrogel Wound Dressings: Where Do We Stand in 2003?, Ostomy Wound Manage, 49(10): 52-57 (2003).

Ellis-Behnke, R. et al, Crystal clear surgery with self-assembling molecules that act as a barrier in the brain and intestine, Abstracts / Nanomedicine: Nanotechnology, Biology, and Medicine, 1:269-270 (2005).

Ellis-Behnke, R., At the nanoscale: nanohemostat, a new class of hemostatic agent, WIREs Nanomedicine and Nanobiotechnology, 3: 70-78 (2011).

English Translation of Office Action for JP2007-520521 (Aug. 24, 2011).

European Search Report for EP 15195734.7, 4 pages (Mar. 4, 2016).

Experimental Report conducted at Arch Therapeutics, $(EAKA)_4$ Acetate, 6 pages, (Jul. 2014).

Experimental Report conducted by Ellis-Behnke, 1. Kidneys (rats), received May 12, 2017.

Extended European Search Report for EP05770153.4, 7 pages (Apr. 7, 2011).

Gervaso, F. et al, The biomaterialist's task: scaffold biomaterials and fabrication technologies, Joints 1(3): 130-137 (2013).

Hilton, J. R. et al, Wound Dressings in Diabetic Foot Disease, Clinical Infectious Diseases, 39: S100-3 (2004).

International Search Report for PCT/US2005/024198, 3 pages (Feb. 23, 2006).

International Search Report for PCT/US2007/025271, 6 pages (Sep. 4, 2008).

International Search Report on Patentability for PCT/US2015/019796, 6 pages, Sep. 13, 2016.

Komatsu, S et al., The Neutral Self-Assembling Peptide Hydrogel SPG-178 as a Topical Hemostatic Agent, PLoS ONE, 9(7): e102778 (2014).

Takei, J., 3-Dimensional Cell Culture Scaffold For Everyone: Drug Screening, Tissue Engineering and Cancer Biology, AATEX, 11(3): 170-176 (2006).

Third Party Observation for EP 05770153.4, with exhibits, 71 pages (Aug. 25, 2014).

Third Party Observation for JP 2008-509090, 43 pages, references in English (Aug. 10, 2011).

Tortora, G. J., Principles of Human Anatomy, Fifth Edition, Chapter 4: The Integumentary System, 98-100 (1989).

Wang. T. et al, Molecular Mechanisms of RAD16-1 Peptide on Fast Stop Bleeding in Rat Models, Int. J. Mol. Sci., 13: 15279-15290 (2012).

Written Opinion for PCT/US2005/024198, 4 pages (Feb. 23, 2006).

Zhang, S. et al, PuraMatrix: Self-Assembling Peptide Nanofiber Scaffolds, Scaffolding in Tissue Engineering, Chapter 15, 217-238 (1992).

Zhang, S. et al, Self-assembling peptides in biology, materials science and engineering, Peptide Science—Present and Future, 737-744 (1999).

Zhang, S. et al, Self-complementary oligopeptide matrices support mammalian cell attachment, Biomaterials, 16(18): 1385-1393 (1995).

Abukawa, H. et al, Reconstructing Mandibular Defects Using Autologous Tissue-Engineered Tooth and Bone Constructs, J. Oral Maxillofac. Surg., 67(2):335-347 (2009).

Allen, P. et al, Type I collagen, fibrin and PuraMatrix matrices provide permissive environments for human endothelial and mesenchymal progenitor cells to form neovascular networks, J. Tissue Eng. Regen Med., 5(4):e74-86 (2011).

Altman, M. et al., Conformational behavior of ionic self-complementary peptides, Protein Sci., 9(6):1095-105 (2000).

Anderson, I. The properties of hyaluronan and its role in wound healing, Prof. Nurse., 17(4):232-5 (2001).

Author Not Known, Medical Devices: Guidance Document, Borderline products, drug-delivery products and medical devices incorporating, as an integral part, an ancillary medicinal substance or an ancillary human blood derivative, European Commission, DG Enterprise and Industry, Directorate F, Unit F3 "Cosmetics and medical devices", 22 pages (Dec. 3, 2009) <http://ec.europa.eu/health/medical-devices/files/meddev/2_1_3_rev_3-12_2009_en.pdf> [last accessed on May 4, 2015].

Bouten, C.V. et al, Substrates for cardiovascular tissue engineering,_ Adv. Drug Deliv. Rev., 63(4-5):221-41 (2011).

Branco, M.C. and Schneider, J.P., Self-assembling materials for therapeutic delivery, Acta. Biomaterialia, 5(3): 817-831 (2009).

Caplan, M.R. et al., Control of self-assembling oligopeptide matrix formation through systematic variation of amino acid sequence, Biomaterials, 23(1):219-27 (2002).

Caplan, M.R. et al., Effects of systematic variation of amino acid sequence on the mechanical properties of a self-assembling, oligopeptide biomaterial, J. Biomater. Sci. Polymer Edn., 13(3):225-236 (2002).

Caplan, M.R. et al., Self-assembly of a beta-sheet protein governed by relief of electrostatic repulsion relative to van der Waals attraction, Biomacromolecules, 1(4):627-31 (2000).

Censi, R. et al, Hydrogels for protein delivery in tissue engineering, J. Control Release, 161(2):680-692 (2012).

Chen, K. et al, A Hybrid Silk/RADA-Based Fibrous Scaffold with Triple Hierarchy for Ligament Regeneration, Tissue Eng. Part A., 18(13-14):1399-409 (2012).

(56) References Cited

OTHER PUBLICATIONS

Chen, P., Self-assembly of ionic-complementary peptides: a physicochemical viewpoint, Colloids and Surfaces A: Physicochemical and Engineering Aspects, 261(1-3): 3-24 (2005).
Cigognini, D. et al, Evaluation of early and late effects into the acute spinal cord injury of an injectable functionalized self-assembling scaffold, PLoS One., 6(5): e19782 (2011).
Concaro, S. et al, Effect of different materials on the proliferation and migration of articular chondrocytes, Osteoarthritis and Cartilage, 15:Supplement B, pp. B119 (2007).
Cooper et al., "Testing the "critical-size" in calvarial bone defects: revisiting the concept of a critical-sized defect (CSD)," Plast Reconstr Surg. 125(6): 1685-1692, 2010.
Cunha, C. et al, Emerging nanotechnology approaches in tissue engineering for peripheral nerve regeneration, Nanomedicine, 7(1):50-59 (2011).
Curley, J.L. et al, Fabrication of micropatterned hydrogels for neural culture systems using dynamic mask projection photolithography, J. Vis. Exp., 48: 2636 (2011).
Davis, M.E. et al, Custom design of the cardiac microenvironment with biomaterials, Circ Res., 97(1):8-15 (2005).
Davis, M.E. et al, Injectable self-assembling peptide nanofibers create intramyocardial microenvironments for endothelial cells, Circulation, 111(4):442-450 (2005).
Davis, M.E. et al, Local myocardial insulin-like growth factor 1 (IGF-1) delivery with biotinylated peptide nanofibers improves cell therapy for myocardial infarction, Proc. Natl. Acad, Sci. USA., 103(21):8155-8160 (2006).
Dutta, R.C. and Dutta, A.K., Comprehension of ECM-Cell dynamics: A prerequisite for tissue regeneration, Biotechnol. Adv., 28(6):764-769 (2010).
Dégano, I.R. et al, The effect of self-assembling peptide nanofiber scaffolds on mouse embryonic fibroblast implantation and proliferation, Biomaterials, 30(6):1156-65 (2009).
Ellis-Behnke, R.G. et al, Nano neuro knitting: peptide nanofiber scaffold for brain repair and axon regeneration with functional return of vision, Proc. Natl. Acad. Sci. USA, 103(13):5054-5059 (2006).
Ellis-Behnke, R.G. et al., Nano hemostat solution: immediate hemostasis at the nanoscale, Nanomedicine, (4):207-215 (2006).
Garreta, E. et al, Osteogenic differentiation of mouse embryonic stem cells and mouse embryonic fibroblasts in a three-dimensional self-assembling peptide scaffold, Tissue Eng., 12(8):2215-27 (2006).
Gelain, F. et al, Slow and sustained release of active cytokines from self-assembling peptide scaffolds, J. Control Release, 145(3):231-239 (2010).
Gelain, F. et al., Designer self-assembling peptide scaffolds for 3-d tissue cell cultures and regenerative medicine, Macromol. Biosci. 7(5):544-551 (2007).
Gherli, T. et al., Comparing warfarin with aspirin after biological aortic valve replacement: a prospective study, Circulation, 110(5):496-500 (2004).
Giri, S. and Bader, A., Improved preclinical safety assessment using micro-BAL devices: the potential impact on human discovery and drug attrition, Drug Discov. Today, 16(9-10):382-397 (2011).
Gonzales, A.L. et al., Integrin interactions with immobilized peptides in polyethylene glycol diacrylate hydrogels, Tissue Eng., 10(11-12):1775-86 (2004).
Guo, H.D. et al, Sustained delivery of VEGF from designer self-assembling peptides improves cardiac function after myocardial infarction, Biochem. Biophys. Res. Commun., 424(1):105-111 (2012).
Guo, H.D. et al, Transplantation of marrow-derived cardiac stem cells carried in designer self-assembling peptide nanofibers improves cardiac function after myocardial infarction, Biochem. Biophys. Res. Commun., 399(1):42-48 (2010).
Guo, J. et al, Reknitting the injured spinal cord by self-assembling peptide nanofiber scaffold, Nanomedicine, 3(4):311-321 (2007).
Gurski, L.A. et al, 3D Matrices for Anti-Cancer Drug Testing and Development, Oncology, Issues Jan./Feb. 2010: 20-25.

Hartgerink, J.D. et al., Peptide-amphiphile nanofibers: a versatile scaffold for the preparation of self-assembling materials, Proc. Natl. Acad. Sci. U S A., 99(8):5133-8 (2002).
Hemmrich, K. et al., Implantation of preadipocyte-loaded hyaluronic acid-based scaffolds into nude mice to evaluate potential for soft tissue engineering, Biomaterials, 26(34):7025-37 (2005).
Henriksson, H. et al, Investigation of different cell types and gel carriers for cell-based intervertebral disc therapy, in vitro and in vivo studies, J. Tissue Eng. Regen. Med., doi: 10.1002/term.480 (2011).
Henriksson, H.B. et al, Transplantation of human mesenchymal stems cells into intervertebral discs in a senogeneic porcine model, Spine (Phila Pa 1976), 34(2):141-148 (2009).
Hollinger, J.O. and Kleinschmidt, J.C., "The critical size defect as an experimental model to test bone repair materials," J. Craniofac Surg 1990(1): 60-68.
Holmes, T.C. et al., Extensive neurite outgrowth and active synapse formation on self-assembling peptide scaffolds, Proc. Natl. Acad. Sci. U S A., 97(12):6728-33 (2000).
Horii, A. et al, Biological designer self-assembling peptide nanofiber scaffolds significantly enhance osteoblast proliferation, differentiation and 3-D migration, PLoS One, 2(2):e190 (2007).
Hsieh, P.C. et al, Controlled delivery of PDGF-BB for myocardial protection using injectable self-assembling peptide nanofibers, J. Clin. Invest., 116(1):237-248 (2006).
Hsieh, P.C.H. et al, Local controlled intramyocardial delivery of platelet-derived growth factor improves postinfarction ventricular function without pulmonary toxicity, Circulation, 114(7):637-644 (2006).
Huang, A.H. et al, Mechanics and mechanobiology of mesenchymal stem cell-based engineered cartilage, J. Biomech., 43(1):128-136 (2010).
Hwang, W. et al., Supramolecular structure of helical ribbons self-assembled from a beta-sheet peptide, The Journal of Chemical Physics, 118(1): 389-397 (2003).
International Search Report for PCT/IB2015/000868, 7 pages (Dec. 8, 2015).
Kates, Declaration of Steven Kates, Ph.D., RE: Japanese Patent Application No. 2008-509090 ("Third Party Declaration") (2012).
Kim, J.H. et al, The enhancement of mature vessel formation and cardiac function in infarcted hearts using dual growth factor delivery with self-assembling peptides, Biomaterials, 32(26):6080-6088 (2011).
Kisiday, J. et al, Self-assembling peptide hydrogel fosters chondrocyte extracellular matrix production and cell division: implications for cartilage tissue repair, Proc. Natl. Acad. Sci. USA, 99(15):9996-10001 (2002).
Kohgo, T. et al, Poster 110: Bone Regeneration for Dental Implants Using Tissue-Engineered Bone With Self-Assembling Peptide Nanofiber 3-Dimensional (3D) Scaffolds, Journal of Oral and Maxillofacial Surgery, 65(9): Supplement, p. 43.e63 (2007).
Kopecek, J. and Yang, J., Peptide-directed self-assembly of hydrogels, Acta Biomaterialia, 5(3): 805-816 (2009).
Kumada, Y. and Zhang, S., Significant type I and type III collagen production from human periodontal ligament fibroblasts in 3D peptide scaffolds without extra growth factors, PLoS One, 5(4):e10305 (2010).
Kumada, Y. et al., Functionalized scaffolds of shorter self-assembling peptides containing MMP-2 cleavable motif promote fibroblast proliferation and significantly accelerate 3-D cell migration independent of scaffold stiffness, Soft Matter, The Royal Society of Chemistry, 7 pages (2010).
Kyle, S. et al., Production of self-assembling biomaterials for tissue engineering, Trends Biotechnol., 27(7):423-33 (2009).
Lampe, K.J. and Heilshorn, S.C., Building stem cell niches from the molecule up through engineered peptide materials, Neurosci. Lett., 519(2):138-46 (2012).
Lee, J. et al., Three-dimensional cell culture matrices: state of the art, Tissue Eng. Part B Rev., 14(1):61-86 (2008).
Leon, E.J. et al., Mechanical properties of a self-assembling oligopeptide matrix, J. Biomater. Sci. Polymer Edn., 9(3):297-312 (1998).
Leung, G.K. et al, Peptide nanofiber scaffold for brain tissue reconstruction, Methods Enzymol., 508:177-190 (2012).

(56) References Cited

OTHER PUBLICATIONS

Li, X. et al, Engineering neural stem cell fates with hydrogel design for central nervous system regeneration, Progress in Polymer Science, 37(8):1105-1129 (2012).

Liedmann, A. et al, Cultivation of human neural progenitor cells in a 3-dimensional self-assembling peptide hydrogel, J. Vis. Exp., (59):e3830 (2012).

Liu, J. et al, Controlled release of paclitaxel from a self-assembling peptide hydrogel formed in situ and antitumor study in vitro, Int. J. Nanomedicine, 6:2143-53 (2011).

Liu, W-M. et al., Diversification of Microfluidic Chip for Applications in Cell-Based Bioanalysis, Chinese Journal of Analytical Chemistry, 40(1): 24-31 (2012).

Loo, Y. et al., From short peptides to nanofibers to macromolecular assemblies in biomedicine, Biotechnol. Adv., 30(3):593-603 (2012).

Luo, Z. and Zhang, S., Designer nanomaterials using chiral self-assembling peptide systems and their emerging benefit for society, Chem. Soc. Rev., 41(13):4736-54 (2012).

Luo, Z. et al, Fabrication of self-assembling d-form peptide nanofiber scaffold d-EAK16 for rapid hemostasis, Biomaterials, 32(8):2013-20 (2011).

Maher, S.A. et al, A nano-fibrous cell-seeded hydrogel promotes integration in a cartilage gap model, J. Tissue Eng. Regen. Med., 4(1):25-29 (2010).

Marini, D.M. et al., Left-Handed Helical Ribbon Intermediates in the Self-Assembly of a beta-Sheet Peptide, Nano Letters, 2(4):295-299 (2002).

Marston, W.A. et al., Initial report of the use of an injectable porcine collagen-derived matrix to stimulate healing of diabetic foot wounds in humans, Wound Repair Regen., 13(3):243-7 (2005).

Masuhara, H. et al, Novel infectious agent-free hemostatic material (TDM-621) in cardiovascular surgery, Ann. Thorac. Cardiovasc. Surg. Methods Enzymol., 18(5):444-451 (2012).

McGrath, A.M. et al, BD ©PuraMatrix® peptide hydrogel seeded with Schwann cells for peripheral nerve regeneration, Brain Res. Bull., 83(5):207-213 (2010).

Meng, H. et al, Peripferal Nerve Regeneration in Response to Synthesized Nanofiber Scaffold Hydrogel, Life Science Journal, 9(1): 42-46 (2012).

Misawa, H. et al, PuraMatrix facilitates bone regeneration in bone defects of calvaria in mice, Cell Transplant, 15(10):903-910 (2006).

Mooney, M.P. and Siegel, M.I., Animal models for bone tissue engineering of critical-sized defects (CSDs), bone pathologies, and orthopedic disease states, In: Hollinger, JO.; Einhorn, TA.; Doll, BA.; Sfeir, C., editors. Bone Tissue Engineering. Boca Raton, FL: C.R.C. Press, pp. 217-244 (2005).

Nakahara, H. et al., Bone repair using a hybrid scaffold of self-assembling peptide PuraMatrix and polyetheretherketone cage in rats, Cell Transplant, 19(6):791-797 (2010).

Narmoneva, D.A. et al, Endothelial cells promote cardiac myocyte survival and spatial reorganization: implications for cardiac regeneration, Circulation, 110(8):962-968 (2004).

Narmoneva, D.A. et al., Self-assembling short oligopeptides and the promotion of angiogenesis, Biomaterials, 26(23):4837-46 (2005).

Nichol, J.W. et al, Co-culture induces alignment in engineered cardiac constructs via MMP-2 expression, Biochem. Biophys. Res. Commun., 373(3):360-365 (2008).

Nishimura, A. et al, Controlled release of insulin from self-assembling nanofiber hydrogel, PuraMatrix®: application for the subcutaneous injection in rats, Eur. J. Pharm. Scl., 45(1-2):1-7 (2012).

Ortinau, S. et al, Effect of 3D-scaffold formation on differentiation and survival in human neural progenitor cells, Biomed. Eng Online, 9(1):70 (2010).

Osterman, D.G. and Kaiser, E.T., Design and characterization of peptides with amphiphilic beta-strand structures, J. Cell Biochem., 29(2):57-72 (1985).

Patterson, J. et al., Biomimetic materials in tissue engineering, Materialstoday, 13(1-2):14-22 (2010).

Saiga, K. et al, Combined use of bFGF and GDF-5 enhances the healing of medial collateral ligament injury, Biochem. Biophys. Res. Commun., 402(2):329-334 (2010).

Sanborn, T.J. et al., A Thermally Triggered, Enzymatically Cross-linked PEG-Peptide Hydrogel for Biomaterial Applications, Presented at 2001 Annual Meeting, Americal Institute of Chemical Engineers, Reno, NV, Nov. 4-9, 2001.

Scalfani, A.P. and Romo III., T., Injectable fillers for facial soft tissue enhancement, Facial Plast. Surg., 16(1):29-34 (2000).

Segers, V.F. and Lee, R.T., Local delivery of proteins and the use of self-assembling peptides, Drug Discov. Today, 12(13-14):561-8 (2007).

Segers, V.F.M. and Lee, R.T., Stem-cell therapy for cardiac disease, Nature 451, 937-942 (2008).

Segers, V.F.M. et al, Local delivery of protease-resistant stromal cell derived factor-1 for stem cell recruitment after myocardial infarction, Circulation, 116(15):1683-1692 (2007).

Semino, C.E. et al., Entrapment of migrating hippocampal neural cells in three-dimensional peptide nanofiber scaffold, Tissue Eng., 10(3-4):643-55 (2004).

Semino, C.E., Self-assembling peptides: from bio-inspired materials to bone regeneration, J. Dent Res., 87(7):606-616 (2008).

Serban, M.A. et al, Effects of extracellular matrix analogues on primary human fibroblast behavior, Acta Biomater., 4(1):67-75 (2008).

Shirai, K. et al, Multipotency of clonal cells derived from swine periodontal ligament and differential regulation by fibroblast growth factor and bone morphogenetic protein, J. Periodontal Res., 44(2):238-247 (2009).

Shivachar, A.C., Isolation and Culturing of Glial, Neuronal and Neural Stem Cell Types Encapsulated in Biodegradable Peptide Hydrogel, Topics in Tissue Engineering, vol. 4. Eds. N Ashammakhi, R Reis, & F Chiellini © 2008.

Song, H. et al, Hemostatic efficacy of biological self-assembling peptide nanofibers in a rat kidney model, Macromol Biosci., 10(1):33-39 (2010).

Spencer, N.J. et al, Peptide- and collagen-based hydrogel substrates for in vitro culture of chick cochleae, Biomaterials, 29(8):1028-1042 (2008).

Sur, S. et al, A hybrid nanofiber matrix to control the survival and maturation of brain neurons, Biomaterials, 33(2):545-55 (2012).

Thonhoff, J.R. et al, Compatibility of human fetal neural stem cells with hydrogel biomaterials in vitro, Brain Res., 1187:42-51 (2008).

Tokunaga, M. et al., Implantation of cardiac progenitor cells using self-assembling peptide improves cardiac function after myocardial infarction, J. Mol. Cell. Cardiol., 49(6):972-983 (2010).

Tokunou, T. et al, Engineering insulin-like growth factor-1 for local delivery, FASEB J., 22(6):1886-1893 (2008).

Uemura, M. et al, Matrigel supports survival and neuronal differentiation of grafted embryonic stem cell-derived neural precursor cells, J. Neurosci. Res., 88(3):542-551 (2010).

Van Putten, S.M. et al, The downmodulation of the foreign body reaction by cytomegalovirus encoded interleukin-10, Biomaterials, 30(5):730-735 (2008).

Wang, Q.G. et al, The composition of hydrogels for cartilage tissue engineering can influence glycosaminoglycan profile, Eur. Cell Mater, 19:86-95 (2010).

Written Opinion for PCT/IB2015/000868, 9 pages (Dec. 8, 2015).

Yamaoka, H. et al, Cartilage tissue engineering using human auricular chondrocytes embedded In different hydrogel materials, J. Biomed. Mater Res. A., 78(1):1-11 (2006).

Ye, Z. et al, Temperature and pH effects on biophysical and morphological properties of self-assembling peptide RADA16-I., J. Pept. Sci., 14(2):152-162 (2008).

Yla-Outinen, L. et al, Three-dimensional growth matrix for human embryonic stem cell-derived neuronal cells, J. Tissue Eng. Regen. Med., doi: 10.1002/term.1512 (2012).

Yokoi, H. et al., Dynamic reassembly of peptide RADA16 nanofiber scaffold, Proc. Nati. Acad. Sci. U S A, 102(24):8414-9 (2005).

Yoshimi, R. et al, Self-assembling peptide nanofiber scaffolds, platelet-rich plasma, and mesenchymal stem cells for injectable bone regeneration with tissue engineering, J. Craniofac. Surg., 20(5):1523-1530 (2009).

(56) References Cited

OTHER PUBLICATIONS

Yu, Y.C. et al., Construction of biologically active protein molecular architecture using self-assembling peptide-amphiphiles, Methods Enzymol., 289:571-87 (1997).
Zarzhitsky, S. and Rapaport, H., The interactions between doxorubicin and amphiphilic and acidic β-sheet peptides towards drug delivery hydrogels, J. Colloid Interface Sci. 360(2):525-531 (2011).
Zhang et al., Building from the Bottom Up, Materials Today, Review Feature, 20-27 (2003).
Zhang et al., Emerging Biological Materials Through Molecular Self-Assembly, Biotechnology Advances, 20: 321-339 (2002).
Zhang, S. Self-assembling peptide materials, Amino Acids, Pept. Proteins, 37:40-65 (2012).
Zhang, S., Beyond the Petri dish, Nat. Biotechnol., 22(2):151-2 (2004).
Zhang, S., Designer Self-Assembling Peptide Nanofiber Scaffolds for Study of 3-D Cell Biology and Beyond, Cancer Research, 335-362 (2008).
Zhang, S., Emerging biological materials through molecular self-assembly, Biotechnol. Adv., 20(5-6):321-39 (2002).
Zhang, S., Fabrication of novel biomaterials through molecular self-assembly, Nat. Biotechnol., 21(10):1171-8 (2003).
Zhang, S., Hydrogels: Wet or let die, Nat. Mater., 3(1):7-8 (2004).
Zhao, X. et al., Recent development of peptide self-assembly, Progress in Natural Science 18, 6(10):653-660 (2008).
Zhaoyang, Y. et al., Temperature and pH effects on biophysical and morphological properties of self-assembling peptide RADA16-T, Journal of Peptide Science, 14(2):152-162 (2008).
Aguado, B. A. et al., Improving Viability of Stem Cells During Syringe Needle Flow Through the Design of Hydrogel Cell Carriers, Tissue Eng Part A., 18(7-8): 806-815. (2012).
Anderson, J. M. et al., Modulating the Gelation Properties of Self-Assembling Peptide Amphiphiles, ACS Nano., 3(11): 3447-3454 (2009).
Deshpande, A. P., Techniques in oscillatory shear rheology. SERC School-cum-Symposium on Rheology of Complex Fluids Jan. 4-9, 2010, Indian Institute of Technology Madras, Chennai, India https://physics.litm.ac.in/-compflu/Lect-notes/abhijit.pdf, accessed online on Jan. 23, 2020, 23 pages (2010).
Gao, J., Self-assembly and Gelation Properties of Novel Peptides for Biomedical Applications, Thesis submitted to University of Manchester for the degree of Doctor in Philosophy. Accessed online at https://www.escholar.manchester.ac.uk/api/datastream?publication Pid=uk-ac-man-scw:200520&datastreamId=FULL-TEXT. PDF on Jan. 14, 2020. 180 pages. (Year: 2013).
Gasiorowski, J. Z., and Collier, J. H., Directed Intermixing in Multicomponent Self-Assembling Biomaterials, Biomacromolecules, 12: 3549-3559 (2011).
Guvendiren, M. et al., Shear-thinning hydrogels for biomedical applications, Soft Matter, 8:260-272 (2012).
Hsu, B. B. et al, Clotting Mimicry from Robust Hemostatic Bandages Based on Self-Assembling Peptides, ACS Nano, 9(9): 9394-9406 (2015).
Meng, H. et al, The effect of a self-assembling peptide nanofiber scaffold (peptide) when used as a wound dressing for the treatment of deep second degree burns in rats, J. Biomed. Mater Res. B. Appl. Biomater., 89(2): 379-91 (2009).
Paradis-Bas, M. et al, RADA-16: A Tough Peptide—Strategies for Synthesis and Purification, Eur. J. Org. Chem., 5871-5878 (2013).
PuraStat® Synthetic Surgical Hemostatic Agent, Product Information, Nanotechnology Products Database, registration date Mar. 30, 2017, retrieved from <<https://product.statnano.com/product/8558>>, accessed on Oct. 11, 2019.
Taghavi, L. et al, Evaluation of the hemocompatability of RADA 16-1 peptide, J. Blomat. App., 32(8): 1024-1031 (2018).
Vader, D. and Wyss, H., Introduction to Rheology, retrieved from <<http://weitzlab.seas.harvard.edu/files/weitzlab/files/introductiontorheology2.pdf>>, accessed online on Jan. 22, 2020, 31 pages (2020).

Xu, F. F. et al, Comparison between self-assembling peptide nanofiber scaffold (SAPNS) and fibrin sealant in neurosurgical herostasis, Clin. Transl. Sci., 8(5): 490-4 (2015).
[No Author Listed] Fluid. Iwanami Rikagaku Dictionary, 3rd edition Incremental version, 2nd Print, Oct. 20, 1981, p. 1430, Partial English Translation, 1 Page.
Akers, M. J., Chapter 26: Parenteral Preparations, Remington: Essentials of Pharmaceutics, Edited by Linda Felton, Pharmaceutical Press, p. 497 (2012).
Arista™ Information Sheet, Medafor, Inc., 6 pages (2006).
Arosio, P. et al, End-to-end self-assembly of RADA 16-I nanofibrils in aqueous solutions, Biophys. J., 102(7): 1617-26 (2012).
Author Unknown, Acrodisc® Syringe Filter with Supor® Membrane -0.2 μm, 13mm (1000/pkg), Product ID: 4692, Pall Shop, accessed from <<https://shop.pall.com/us/en/laboratory/sterile-filtration-and-clarification/mycoplasma-reduction/acrodisc-syringe-filters-with-supor-membrane-zid4692>> (2019).
Author Unknown, AORNs Recommended Practices for Maintaining a Sterile Field Is Up for Review and Public Comment Through Mar. 25, 2005, retrieved from <<https://www.infectioncontroltoday.com/guidelines/aorns-recommended-practices-maintaining-sterile-field-review-and-public-comment-through>>, accessed on Dec. 19, 2018 (23 pages).
Author Unknown, ISO 13485, Wikipedia, retrieved from <<https://en.wikipedia.org/w/index.php?title=IS0 13485&oldid=694123721>> Accessed on Dec. 2, 2016.
Author Unknown, Medical Device, Wikipedia, retrieved from <<https://en.wikipedia.org/w/index.php?title=Medical_device&oldid=699710004>>, retrieved on Dec. 2, 2016.
Basford, P.J., et al., Endoscopic resection of sporadic duodenal adenomas: comparison of endoscopic mucosal resection (EMR) with hybrid endoscopic submucosal dissection (ESD) techniques and the risks of late delayed bleeding, Surg. Endosc., 28: 1594-1600 (2014).
Baumfalk and Finazzo, Filter Integrity testing helps to ensure that GMP sterility requirements are met, BioPharm International, 19(6): 1-3 (2006).
Beam, J., Wound Cleansing: Water or Saline?, Journal of Athletic Training, 41(2): 196-197 (2006).
Becton, Dickinson and Company, Positively Unique: BD PosiFlush™ Pre-Filled Syringes, Brochure, 6 pages (Jun. 2010).
Boyle, A. L., Applications of de novo designed peptides, Peptide Applications in Biomedicine, Biotechnology and Bioengineering, 51-86 (2017).
Chambers, J. et al, Memorandum regarding Nucleic Acid and Peptide Claim Interpretation: "A" and "The," USPTO, 2 pages. Dec. 29, 2005.
CoSeal® Surgical Sealant, Information Sheet, Baxter Healthcare Corporation, 8 pages (2006).
CRYOLIFE®, Life Restoring Technologies, BioGlue® Instructions for Use: Surgical Adhesive Syringe Instructions for Use, L6312. 008—(Apr. 2014), pp. 1-15, 16 pages (2014).
Cunha, C. et al., 3D culture of adult mouse neural stem cells within functionalized self-assembling peptide scaffolds, International Journal of Nanomedicine, 943-955 (2011).
CyroLife: BioGlue® Surgical Adhesive, Products & Services, Website © 2007-2012,<http://web.archive.org/web/20120226221438/http://cryolife.com/products/bioglue-surgical-adhesive>, Retrieved Sep. 1, 2017.
Dojindo catalog,—SulfoBiotics—Sodium sulfide (Na2S), retrieved from http://www.dojindo.eu.com/store/p/685-SulfoBiotics-Sodium-sulfide-Na2S.aspx. 2 pages, downloaded Apr. 25, 2018.
Driscoll, P., What are the differences and similarities between laparoscopy and endoscopy?, 1 page (2016), <https//www.quora.com/what-are-the-differences-and-simliarities-between-laparoscopy-and-endoscopy> Retrieved on Oct. 4, 2017.
Ginsberg, M., Good Medicine/Bad Medicine And The Law Of Evidence: Is There A Role For Proof Of Character, Propensity, Or Prior Bad Conduct In Medical Negligence Litigation?, South Caroline Law Review, 63:367-402 (2011).
Hielscher Ultrasound Technology, 2008, Ultrasonic Degassing and Defoaming of Liquids, accessed from https://www.hielscher.com/degassing_01.htm, on Mar. 27, 2019.

(56) References Cited

OTHER PUBLICATIONS

Hirai, K. et al, The fundamental study of Matrigel (PuraMatrix TM) for the hemostasis of bleeding from pulmonary artery and vein or the prevention of lung fistel, Gen Thorac Cardiovasc Surg, 59 (Supplement): 600 (2011).
Ingenito, E. P. et al, Bronchoscopic Lung Volume Reduction in Severe Emphysema, Proc. Am. Thorac Soc., 5(4): 454-460 (2008).
InjectorForce Max™, Olympus, Brochure, 3 pages (2012).
Koh, R., et al. Antithrombotic drugs are risk factors for delayed postoperative bleeding after endoscopic submucosal dissection for gastric neoplasms, Gastrointest. Endosc., 78: 476-483 (2013).
Kubba, A.K. and Palmer, K. R., Role of endoscopic injection therapy in the treatment of bleeding peptic ulcer, British Journal of Surgery, 83: 461-468 (1996).
Kyle, S. et al, Recombinant self-assembling peptides as biomaterials for tissue engineering, Biomaterials, 31: 9395-9405 (2010).
Lao, W., Repair Medical Science and Tissue Engineering, Chemical Industry Press, 1st ed., pp. 91-93 (2003). [Chinese].
Lin, H-J. et al, A prospective, randomized trial of large-versus small-volume endoscopic injection of epinephrine for peptic ulcer bleeding, Gastrointestinal Endoscopy, 55(6): 615-619 (2002).
Louie, M. K. et al, Bovine Serum Albumin Glutaraldehyde for Completely Sutureless Laparoscopic Heminephrectomy in a Survival Porcine Model, Journal of Endourology, 24(3): 451-455 (2010).
Lépilliez, V., et al., Endoscopic resection of sporadic duodenal adenomas: an efficient technique with a substantial risk of delayed bleeding, Endoscopy, 40: 806-810 (2008).
McFadden, P. M., Minimally Invasive Thoracic Surgery, vol. 2, No. 3, Jul. 2000, pp. 137-144.
Mimotopes, A Guide to Handling and Storing Peptides, PU3-004-1, Feb. 20, 2011, Date established via internet achieve http://www.mimotopes.com/files/editor_upload/File/PeptidesAndAntibodies/PU3004-1Handling-and-Storing-Peptides.PDF.
Moser, C. et al, Autologous fibrin sealant reduces the incidence of prolonged air leak and duration of the chest tube drainage after lung volume reduction surgery: a prospective randomized blinded study, Journal of Thoracic and Cardiovascular Surgery, 136(4): 843-849 (2008).
Olson. E. J., Hyperinflated Lungs: What does it mean?, A recent chest X-ray showed that I have hyperinflated lungs. What could cause this?, Mayo Clinic, Nov. 30, 2017, retrieved from <<https://www.mayoclinic.org/diseases-conditions/emphysema/expert-answers/hyperinflated-lungs/faq-20058169>>, 3 pages, accessed Feb. 14, 2019.
Ono, S. et al., Thienopyridine derivatives as risk factors for bleeding following high risk endoscopic treatments: Safe Treatment on Antiplatelets (STRAP) study, Endoscopy, 47: 632-637 (2015).
Paramasivam. E., Air leaks, pneumothorax, and chest drains, Continuing Education in Anaesthesia, Critical Care & Pain. vol. 8 No. 6 2008.
Pioche, M. et al, A self-assembling matrix-forming gel can be easily and safely applied to prevent delayed bleeding after endoscopio resections, Endoscopy International Open, 4: E415-E419 (2016).
Reich, I. et al., Chapter 36: Tonicity, Osmoticity, Osmolality, and Osmolarity, Remington: Practice of The Science and Pharmacy, 19th edition, Mack Publishing Company, 613-621 (1995).
Sigma-Aldrich catalog, Sodium Bicarbonate, retrieved from https://www.sigmaaldrich.com/catalog/product/sigma/s5761?lang=en&region=US, 4 pages, downloaded on Apr. 25, 2018.
Spotnitz, W. D. and Banks, S., Hemostats, sealants and adhesives: components of the surgical toolbox, Transfusion, 48: 1502-1516 (2008).
Stark, J. and De Leval, M., Experience with fibrin seal (Tisseel) in operations for congenital heart defects, Ann. Thorac, Surg., 38(4):411-3 (1984).
Stiuso, P. et al., The self-association of protein SV-IV and its possible functional implications, Eur. J. Biochem., 266(3):1029-35 (1999).
Sun-Sri, TITAN2® 17mm filter, 2009, accessed from https://sun-sri.com/products/17mm_filters.aspx, accessed on May 22, 2019.
Tam, J. et al., Fractional skin harvesting: autologous skin grafting without donor-site morbidity, Plastic and Reconstructive Surgery Global Open, 1(6): e47 (2013).
The University of Waterloo, Buffer Solutions, retrieved from https://web.archive.org/web/20001213162000/http://www.science.uwaterloo.ca/-cchieh/cact/c123/buffer.htm, 6 pages, downloaded on Apr. 24, 2018.
Thermo Scientific, MaxQ 2000 Open-Air Platform Shaker, 30 pages (2010).
Week 201413 Thomson Scientific, London, GB: AN 2013-U98585, XP0027 40500, Use of nigella glandulifera freyn 3 seed grass volatile oil for preparing medicine for treating chronic obstructive pulmonary disease, & CN 103 251 690 A People's Liberation Army Xinjiang Milita) Aug. 21, 2013 (Aug. 21, 2013) abstract.
Whatman Product Guide, 2 pages (1997).
Wu, M. et al., Self-assembling peptide nanofibrous hydrogel on immediate hemostasis and accelerative osteosis, Biomacromolecules, 16: 3112-3118 (2015).
Wu. X. et al, Functional self-assembling peptide nanofiber hydrogel for peripheral nerve regeneration, Regenerative Biomaterials, 21-30 (2016).
Yamamoto, H. et al, A novel method of endoscopic mucosal resection using sodium hyaluronate, Gastrointestinal Endoscopy, 50(2): 251-256 (1999).
Yoshida, M, et al., Initial clinical trial of a novel hemostat, TDM-621, in the endoscopic treatments of the gastric tumors, J. Gastroenterol Hepatol., 29: 77-79 (2014).
Zhou, X-R. et al., Self-assembly of PH and calcium dual-responsive peptide-amphiphiic hydrogel, Journal of Peptide Science, 19: 737-744 (2013).
3-D Matrix Japan, Ltd. Company Profile Power Point, 32 pages, May 2006 (with English translation).
3D Matrix Japan, Company, Technology, Products, Technology, FAQs, Publication, Company, News, Contact, no English translation, 17 pages. URL: http://www.3d-matrix.co.jp/cm02.html [Retrieved Ferbaruy 25, 2005].
3D Matrix Japan, Product Features, with English translation. 2 pages. URL: http://web.archive.org/web/20050416044014/http://www.3d-matrix.eo.jp/pr03.html [Retrieved Feb. 20, 2013].
3D Matrix Japan, Product List, with English translation, 2 pages. URL: http://web.archive.org/web/20050416043834/http://www.3d-matrix.co.jp/pr02.html [Retrieved Aug. 1, 2013].
3D Matrix Japan, Products, with English translation, 2 pages. URL: http://web.archive.org/web/20050415004502/http://www.3d-matrix.eo.jp/pr01.html [Retreived Feb. 20, 2013].
Davis, M.E. et al., Injectable self-assembling peptide nanofibers create intramyocardial microenvironments for endothelial cells, Circulation, 111(4):442-50 (2005).
Dégano, J.R. et al, The effect of self-assembling peptide nanofiber scaffolds on mouse embryonic fibroblast implantation and proliferation, Biomaterials, 30(6):1156-65 (2009).
Ellis-Behnke, R.G. et al., Nano hemostat solution: immediate hemostasis at the nanoscale, Nanomedicine, 2(4):207-15 (2006).
Gelain, F. et al., Designer self-assembling peptide scaffolds for 3-d tissue cell cultures and regenerative medicine, Macromol. Biosci., 7(5):544-51 (2007).
Gelain, F. et al., Slow and sustained release of active cytokines from self-assembling peptide scaffolds, Journal of Controlled Release, 145:231-239 (2010).
Hemmrich, K. et al., Implantation of preadipocyte-loaded hyaluronic acid-based scaffolds into nude mice to evaluate potential for soft tissue engineering, Biomaterials, 26(34):7025-37 (2005).
International Search Report for PCT/US2005/024198, 3 pages (Feb. 23, 2008).
Kates, Declaration of Steven Kales, Ph.D., RE: Japanese Patent Application No. 2008-509090 ("Third Party Declaration") (2012).
Kim, J.H. et al, The enhancement of mature vessel formation and cardiac function in infarcted hearts using dual growth factor delivery with self-assembling peptides, Biomaterials, 32(26):6080-6068 (2011).

(56) References Cited

OTHER PUBLICATIONS

Kumada, Y. and Zhang, S., Significant type I and type III collagen production from human periodontal ligament fibroblasts in 3D peptide scaffolds without extra growth factors, PLoS One, 5(4):e10305 (2010).

Lee. J. et al., Three-dimensional cell culture matrices: state of the art, Tissue Eng. Par B Rev., 14(1):61-86 (2008).

Liu. J. et al., Controlled release of paclitaxel from a self-assembling peptide hydrogel formed in situ and antitumor study in vitro, International Journal of Nanomedicine, 6:2143-2153 (2011).

Misawa, H. et al, PuraMatrix facilitates bone regeneration in bone detects of calvaria in mice, Cell Transplant, 15(10):903-910 (2006).

Nishimura, A. et al., Controlled release of insulin from self-assembling nanofiber hydrogel, PuraMatrix: application for the subcutaneous injection in rats, European Journal of Pharmaceutical Sciences, 45:1-7 (2012).

Third Part Observation for EP 05770153.4, with exhibits, 71 pages (Aug. 25, 2014).

Ye, Z. et al., Temperature and pH effects on biophysical and morphological properties of self-assembling peptide RADA16-I, J. Pept. Sci., 14(2):152-62 (2008).

Yokoi, H. et al., Dynamic reassembly of peptide RADA16 nanofiber scaffold, Proc. Natl. Acad. Sci. U S A, 102(24):8414-9 (2005).

Zhang, S. Sell-assembling peptide materials, Amino Acids, Pept. Proteins, 37:40-65 (2012).

\* cited by examiner

STERILIZATION AND FILTRATION OF PEPTIDE COMPOSITIONS

CROSS REFERENCE TO RELATED APPLICATIONS

This application is a divisional application of U.S. patent application Ser. No. 15/122,749 filed Aug. 31, 2016, which a U.S. National Stage Application filed under 35 U.S.C. § 371 based on International Application No. PCT/IB15/00868, filed Mar. 10, 2015, which claims benefit under 35 U.S.C. § 119(e) of U.S. provisional patent application Ser. No. 61/950,536, filed Mar. 10, 2014, the entire contents of each of which are hereby incorporated by reference.

SEQUENCE LISTING

This application makes reference to a sequence listing submitted in electronic form as an ASCII .txt file named "2004837-0108_Sequences.txt". The .txt file was generated on Jun. 19, 2018 and is 1 kb in size. The entire contents of the Sequence Listing are herein incorporated by reference.

BACKGROUND

Peptide agents with the ability to self-assemble into gel structures have a wide variety of uses in therapeutic and research contexts. One such peptide agent, for example, a synthetic, 16-amino acid polypeptide with a repeating sequence of arginine, alanine, and aspartic acid (i.e., RADARADARADARADA [SEQ ID NO:1], also known as "RADA16"), is commercially available under the trade names PuraStat®, PuraMatrix®, and PuraMatrix GMP® from 3-D Matrix Medical Technology, and has demonstrated utility in a wide range of laboratory and clinical applications, including cell culture, drug delivery, accelerated cartilage and bone growth, and regeneration of CNS, soft tissue, and cardiac muscle, and furthermore as a matrix, scaffold, or tether that can be associated with one or more detectable agents, biologically active agents, cells, and/or cellular components.

SUMMARY

The present invention provides, among other things, methods for handling peptide compositions and technologies relating thereto. Teachings provided herein may be particularly applicable to high-viscosity peptide compositions, and/or compositions of self-assembling peptides.

Among other things, the present disclosure demonstrates that certain peptide compositions (e.g., compositions of particular peptides, at particular concentrations, and/or having particular rheological properties) have certain characteristics and/or may not be amenable to certain handling and/or processing steps such as, for example, filtration (e.g., sterilizing filtration).

The present disclosure also demonstrates that certain particular peptide compositions are surprisingly stable to one or more treatments (e.g., heat treatment, as is applied in autoclave procedures) that damage many peptide compositions.

Thus, the present disclosure provides a variety of technologies relevant to processing of peptide compositions, and particularly to sterilization.

In some embodiments, the present disclosure demonstrates that particular peptide compositions may have one or more useful and/or surprising characteristics (e.g., resistance to damage from heat treatment, rheological responsiveness to and/or recovery from application of shear stress, etc.).

The present disclosure provides, among other things, systems for sterilizing peptide compositions, and/or systems for determining appropriate such systems for application to particular peptide compositions.

In some embodiments, particular peptide compositions may be defined, for example, by one or more features selected from the group consisting of: peptide sequence, peptide concentration, viscosity, stiffness, sensitivity to heat treatment, rheological responsiveness to application of shear stress, rheological recovery from application of shear stress, etc.).

Among other things, the present disclosure provides certain peptide compositions that may be sterilized by autoclave treatment.

In some embodiments, the present disclosure provides certain technologies for achieving filtration of certain peptide compositions, and particularly for altering rheological properties of peptide compositions (as defined by identity and sequence of the peptide) so that they are rendered amenable to filtration. For example, in some embodiments, viscosity of peptide compositions to be filtered may be reduced prior to filtration. In some embodiments, shear stress may be applied to peptide compositions, so that rheological properties may be altered. For example, viscosity and/or stiffness of a peptide composition may be reduced prior to filtration; in some embodiments, such a reduction is temporary.

In some embodiments, provided technologies enable filtration of peptide compositions at higher concentrations than is feasible with conventional filtration techniques. For example, technologies described herein permit RADA16 (SEQ ID NO:1) to be filtered, and particularly to be sterilized by filtration, at concentrations higher than 2.5% in accordance.

In some particular embodiments, the present disclosure provides a method for sterilizing a liquid peptide composition whose sequence comprises a series of repeating units of IEIK comprising subjecting the composition to autoclave treatment. In some embodiments, a method does not involve sterilizing filtration.

In some embodiments, the present disclosure provides a method for sterilizing a liquid peptide composition whose sequence comprises a series of repeating units of IEIK (SEQ ID NO:6) comprising subjecting the composition to heat treatment. In some embodiments, the heat treatment performs at about 121° C. for about 25 min.

In some embodiments, the present disclosure provides a method for sterilizing a liquid peptide composition having an initial storage modulus within the range of about 300 to about 5,000 Pa at 1 Pa of oscillation stress, the method comprising steps of subjecting the composition to high shear stress so that storage modulus of the composition is temporarily reduced to a level within a range of about 0.01% to 80% of the initial storage modulus, and subjecting the composition to filtration while its viscosity is at the reduced level.

In some embodiments, the step of subjecting the composition to high shear stress utilizes at least one shear-thinning unit.

In some embodiments, at least one shear-thinning unit is or comprises at least one needle. In some embodiments, at least one needle is at least 10 mm long. In some embodiments, at least one needle has a gauge within the range of about 25 to about 35.

In some embodiments, at least one shear-thinning unit is or comprises at least one screen with micro- or nano-sized holes. In some embodiments, micro- or nano-sized holes have a largest dimension within a range of about 0.5 µm to about 200 µm. In some embodiments, a pinch between holes is about 5 µm to about 10 mm. In some embodiments, a screen is made at least in part of a material selected from the group consisting of stainless-steel, tungsten, titanium, silicon, ceramic, plastic, and combination thereof. In some embodiments, thickness of the screen is about 10 µm to about 10 mm.

In some embodiments, at least one shear-thinning unit is or comprises at least one membrane with micro- or nano-sized pores. In some embodiments, the pores gave a size with a range of about 0.45 µm to about 120 µm.

In some embodiments, high shear stress for sterilization is with a range of about 30 to about 200 Pa.

In some embodiments, a liquid peptide composition comprises RADA16 (SEQ ID NO:1), IEIK13 (SEQ ID NO:3), or KLD12 (SEQ ID NO:2).

In some embodiments, a liquid peptide composition is pressurized prior to filtration. In some embodiments, a peptide liquid composition is further stored the under vacuum.

BRIEF DESCRIPTION OF THE DRAWING

FIG. 1A depicts mass spectrometry before autoclave treatment. FIG. 1B depicts mass spectrometry after autoclave treatment.

FIG. 2A depicts mass spectrometry before autoclave treatment. FIG. 2B depicts mass spectrometry after autoclave treatment.

FIG. 3A depicts mass spectrometry before autoclave treatment. FIG. 3B depicts mass spectrometry after autoclave treatment.

FIGS. 15A, 15B and 15C show features of an exemplary shear thinning unit, a micro-hole screen, which may be used in the device shown in FIG. 13. Holes were generated by laser-drilling technology. Such a screen may be inserted in the first chamber to reduce viscosity of peptide solutions before actual filtration through the membrane in the second chamber. FIG. 15D shows visual observation of viscosity after applying shear stress to 2.5% KLD12 (SEQ ID NO:2) using a micro- or nano-hole screen.

DEFINITIONS

Figure 1A:
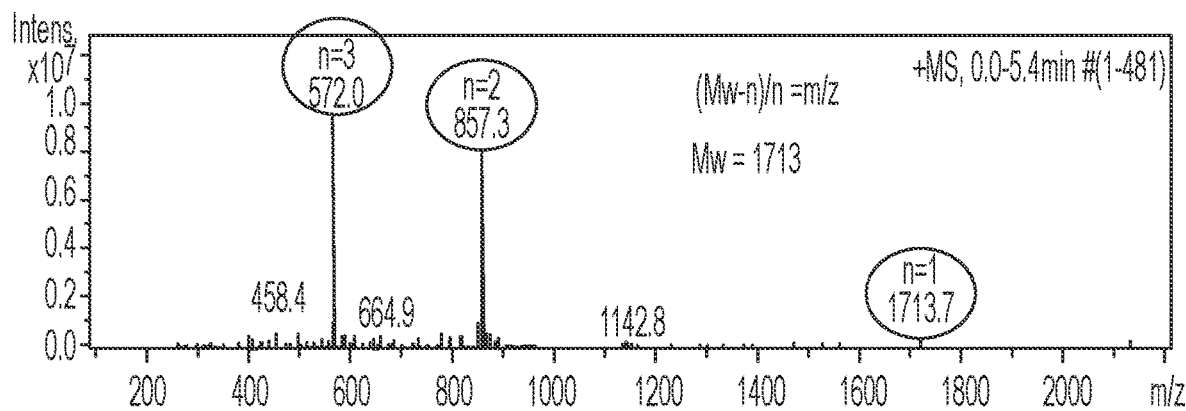
FIGS. 1A and 1B show exemplary mass spectrometry analysis of RADA16 (SEQ ID NO:1) before and after autoclave treatment, to assess heat sensitivity.

The term "agent" as used herein may refer to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

As used herein, the term "amino acid," in its broadest sense, refers to any compound and/or substance that can be incorporated into a polypeptide chain, e.g., through formation of one or more peptide bonds. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Two events or entities are "associated" with one another, as that term is used herein, if the presence, level and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc) will typically refer to comparisons made under comparable conditions.)

Certain methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

The term "gel" as used herein refers to viscoelastic materials whose rheological properties distinguish them from solutions, solids, etc. In some embodiments, a composition is considered to be a gel if its storage modulus (G') is larger than its modulus (G"). In some embodiments, a composition is considered to be a gel if there are chemical or physical cross-linked networks in solution, which is distinguished from entangled molecules in viscous solution.

The term "in vitro" as used herein refers to events that occur in an artificial environment, e.g., in a test tube or reaction vessel, in cell culture, etc., rather than within a multi-cellular organism.

The term "in vivo" as used herein refers to events that occur within a multi-cellular organism, such as a human and a non-human animal. In the context of cell-based systems, the term may be used to refer to events that occur within a living cell (as opposed to, for example, in vitro systems).

The term "peptide" as used herein refers to a polypeptide that is typically relatively short, for example having a length of less than about 100 amino acids, less than about 50 amino acids, less than 20 amino acids, or less than 10 amino acids.

The term "polypeptide" as used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

The term "reference" as used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

DETAILED DESCRIPTION OF CERTAIN EMBODIMENTS

The present invention provides technologies for sterilization of peptide compositions. In some embodiments, disclosed methods are particularly applicable to peptide solutions with high viscosity and/or stiffness. In some embodiments, the present disclosure defines particular peptide solutions that may be sterilized by autoclave treatment. In some embodiments, the present disclosure defines particular peptide solutions that may not be amenable to filtration unless and until treated so as to alter their rheological properties. In some embodiments, the present disclosure provides technologies that may temporarily reduce peptide solution viscosity and/or stiffness sufficiently to permit filtration. In some embodiments, the present disclosure teaches technologies for facilitating handling, processing, and/or filtration of certain peptide solutions, for example by applying high shear stress that modify rheological properties thereof.

Peptides and Peptide Compositions

In accordance with one or more embodiments, peptide compositions to which teachings of the present disclosure may be compositions of amphiphilic peptides having about 6 to about 200 amino acid residues. In certain embodiments, a relevant peptide may have a length of at least about 7 amino acids. In certain embodiments, a peptide may have a length of between about 7 to about 17 amino acids. In certain embodiments, a peptide may have a length of at least 8 amino acids, at least about 12 amino acids, or at least about 16 amino acids.

In some embodiments, as is understood in the art, an amphiphilic polypeptide is one whose sequence includes both hydrophilic amino acids and hydrophobic amino acids. In some embodiments, such hydrophilic amino acids and hydrophobic amino acids may be alternately bonded, so that the peptide has an amino acid sequence of alternating hydrophilic and hydrophobic amino acids. In some embodiments, such a peptide has an amino acid sequence that is or comprises repeats of Arg-Ala-Asp-Ala (RADA; SEQ ID NO:4); in some embodiments, such a peptide has an amino acid sequence that is or comprises repeats of Lys-Leu-Asp-Leu (KLDL; SEQ ID NO:5); in some embodiments, such a peptide has an amino acid sequence that is or comprises repeats of Ile-Glu-Ile-Lys (IEIK; SEQ ID NO:6).

In some embodiments, a peptide for use in accordance with the present disclosure, may generally be self-assembling, and/or may exhibit a beta-sheet structure in aqueous solution under certain conditions.

In some embodiments, a peptide for use in accordance with the present disclosure has an amino acid sequence as found in the commercial product known as PuraMatrix®, i.e., has the amino acid sequence Arg-Ala-Asp-Ala-Arg-Ala-Asp-Ala-Arg-Ala-Asp-Ala-Arg-Ala-Asp-Ala (i.e., RADA16, aka (RADA)$_4$; SEQ ID NO:1). In some embodiments, a peptide for use in accordance with the present disclosure has an amino acid sequence: Lys-Leu-Asp-Leu-Lys-Leu-Asp-Leu-Lys-Leu-Asp-Leu (i.e., KLDL12, aka (KDLD)$_3$, aka KLD12; SEQ ID NO:2). a peptide for use in accordance with the present disclosure has an amino acid sequence: Ile-Glu-Ile-Lys-Ile-Glu-Ile-Lys-Ile-Glu-Ile-Lys-Ile (i.e., IEIK13, aka (IEIK)$_3$I; SEQ ID NO:3).

In some embodiments, peptide compositions to which the present disclosure may be relevant are those characterized by certain rheological properties. In some embodiments, relevant rheological properties may be or include loss modulus, stiffness, rheological recovery time, storage modulus, viscosity, yield stress, etc. In some embodiments, rheological properties are assessed via measurement; in some embodiments, one or more rheological properties may be assessed via visual observation.

In certain embodiments, storage modulus and stiffness have a positive correlation; in general, those of ordinary skill appreciate that higher storage modulus is related to higher stiffness.

In some embodiments, a high viscosity peptide composition is characterized by a storage modulus within the range of about 300 to about 5,000 Pa at 1 rad/sec of frequency and 1 Pa of oscillation stress.

In some embodiments, a peptide composition for use in accordance with the present invention has a peptide concentration within the range of about 0.01% to about 10%.

In some embodiments, a peptide composition to which one or more of the methodologies described herein is applied is of a commercial-scale volume.

In some embodiments, a peptide composition to which one or more of the methodologies described herein is applied is one that has been stored for a period of time. In some embodiments, a peptide composition has been stored in a pressure vessel.

In some embodiments, a peptide composition to which one or more methodologies described herein is applied is then stored, for example, in a reservoir vessel prior to packaging.

Improving Properties

The present disclosure appreciates that preparation and/or handling of certain peptide compositions (e.g., particularly compositions of certain self-assembling peptides and/or of high peptide concentrations) has been complicated by difficulties related, for example, to high viscosity and/or stiffness. The present disclosure particularly demonstrates that certain peptide compositions are not amenable to filtration, and in particular to filtration through sterilizing filters.

The present disclosure further appreciates that filtration challenges can complicate or preclude sterilization of such peptide compositions. The present disclosure provides technologies that permit filtration of certain peptide compositions and/or otherwise permit sterilization.

Autoclave Treatment

Autoclave treatment is a conventional sterilization method that involves subjecting materials to high pressure saturated steam at 121° C. It is generally understood in the art that application of high heat, such as is involved in autoclave treatment, can degrade peptides.

The present disclosure surprisingly demonstrates that certain peptide compositions are stable to heat treatment, and particularly to autoclave treatment. Among other things, the present disclosure demonstrates that such peptide compositions may be sterilized with the autoclave treatment. In some embodiments, such compositions may be sterilized by heat treatment at about 121° C. for about 25 minutes.

In some embodiments, peptide compositions that may be subjected to heat treatment, and/or to autoclave treatment are IEIK13 (SEQ ID NO:3) compositions. In some such embodiments, IEIK13 (SEQ ID NO:3) compositions have a concentration within the range of about 0.01% to about 10%

In some embodiments, peptide compositions that may be subjected to heat treatment and/or to autoclave treatment are KLD12 (SEQ ID NO:2) compositions. In some embodiments, however, KLD12 (SEQ ID NO:2) compositions are not subjected to autoclave treatment in accordance with the present invention.

In some embodiments, RADA16 (SEQ ID NO:1) compositions are not subjected to autoclave treatment in accordance with the present invention.

Without wishing to be bound by any particular theory, the present disclosure proposes that the stability of certain IEIK13 (SEQ ID NO:3) compositions to heat treatment such as autoclave treatment may be attributable, at least in part, to the absence of aspartic acid (Asp, D) in compositions, while RADA16 (SEQ ID NO:1) and KLD12 (SEQ ID NO:2) have aspartic acids.

In some embodiments, peptide compositions that can appropriately be subjected to heat treatment such as autoclave treatment in accordance with the present invention are characterized by resistance to degradation when exposed to such treatment and/or by stability of rheological properties (e.g., viscosity and/or stiffness) when subjected to such treatment. In accordance with the present disclosure, peptide compositions of interest may be exposed to heat treatment such as autoclave treatment, and one or more properties of the composition (e.g., peptide degradation and/or one or more rheological properties) can be assessed, for example before and after treatment, so that appropriateness of sterilizing such composition via autoclave treatment may be determined (see, e.g., Example 2).

Rheological Property Alteration

The present disclosure demonstrates that certain peptide compositions can be rendered amenable to filtration via exposure to treatment that alters one or more rheological properties (e.g., that alters viscosity and/or stiffness).

In some particular embodiments, rheological property alteration is achieved by exposure to shear stress.

Without wishing to be bound by any particular theory, the present disclosure proposes that subjecting peptide compositions as described herein to high shear stress can disrupt self-assembled structures. The present disclosure further proposes that recovery time may represent that required for such structures to re-form.

In some embodiments, shear stress applied to peptide solutions may be at least about 20 Pa. In some embodiments, shear stress applied to peptide solutions may be at least about 30 Pa. In some embodiments, shear stress applied to peptide solutions may be at least about 40 Pa. In some embodiments, shear stress applied to peptide solutions may be at least about 50 Pa. In some embodiments, shear stress applied to peptide solutions may be at least about 60 Pa. In some embodiments, shear stress applied to peptide solutions may be at least about 60 Pa. In some embodiments, shear stress applied to peptide solutions may be at least about 80 Pa. In some embodiments, shear stress applied to peptide solutions may be at least about 90 Pa. In some embodiments, shear stress applied to peptide solutions may be at least about 100 Pa. In some embodiments, the amount of shear stress may be at least about 30~100 Pa, for example, in view of the yield stress of RADA16 (SEQ ID NO:1) 2.5%, IEIK13 (SEQ ID NO:3) 1.5% and 2.5% and KLD12 (SEQ ID NO:2) 2.5% noted above.

In some embodiments, viscosity of peptide solutions may drop significantly with shear stress. In some embodiments, viscosity of peptides solutions may drop at least 10% with shear stress. In some embodiments, viscosity of peptides solutions may drop at least 30% with shear stress. In some embodiments, viscosity of peptides solutions may drop at least 50% with shear stress. In some embodiments, viscosity of peptides solutions may drop at least 70% with shear stress. In some embodiments, viscosity of peptides solutions may drop at least 90% with shear stress.

In some embodiments, the rheological property alteration is temporary. In some embodiments, the peptide composition is characterized by rheological recovery characteristics. For example, in some embodiments, such compositions are characterized in that one or more of their rheological properties are restored within a time period within a range of about 1 min to about 48 hours.

In some embodiments, rheological restoration is considered to be achieved when one or more rheological properties return to a level at least 20% of its initial value.

In some embodiments, rheological restoration is considered to be achieved when the change observed in one or more rheological properties upon application of shear stress is at least 30% reversed.

In some embodiments, peptide compositions may recover their storage modulus after application of shear stress. In some embodiments, peptide solutions may recover about 0.1 to 100% of their original storage modulus in 1 min. In some embodiments, peptide solutions may recover about 0.1 to 10% of their original storage modulus in 1 min. In some embodiments, peptide solutions may recover about 20 to 100% of their original storage modulus in 20 min. In some embodiments, peptide solutions may recover about 20 to 60% of their original storage modulus in 20 min.

In some embodiments, peptide solutions may recover their viscosity over time after filtration. In some embodiments, peptide solutions may recover about 0.1 to 30% of their original viscosity in 1 min. In some embodiments, peptide solutions may recover about 0.1 to 100% of their original viscosity in 1 min. In some embodiments, peptide solutions may recover about 20 to 100% of their original viscosity in 20 min. In some embodiments, peptide solutions may recover about 20 to 60% of their original viscosity in 20 min.

Figure 10:
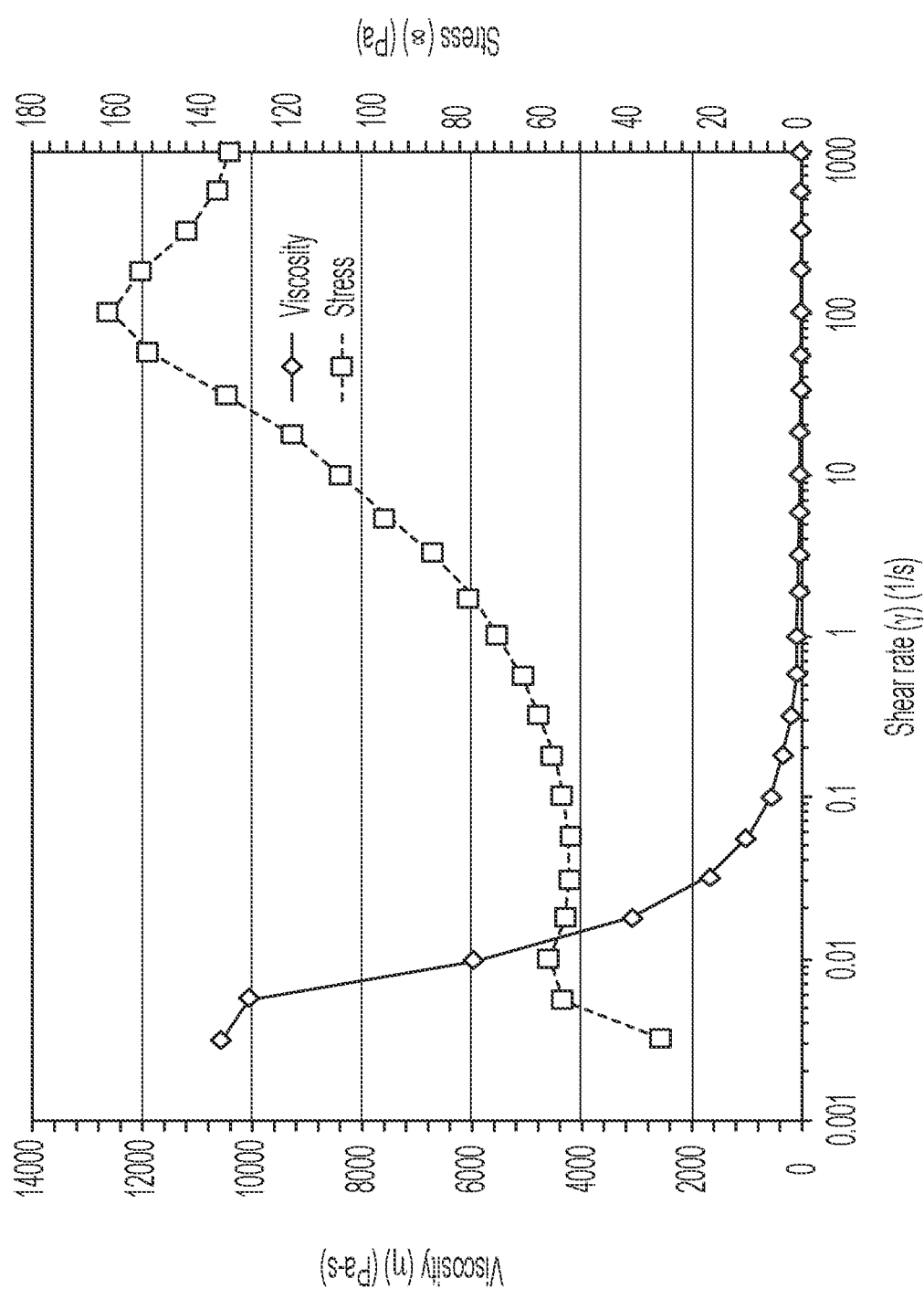
FIG. 10 shows an exemplary flow viscosity test performed from 0.003 to 1000 1/sec of shear rate on 1.5% IEIK13 (SEQ ID NO:3) solution.

The present disclosure specifically exemplifies appropriate adjustment of rheological properties of certain peptide compositions upon application of shear stress (e.g., specifically upon passage through a needle, for example of particular structure) (see Example 4). The results presented in this Example show a logarithmic increase of storage modulus from 1 minute after injection, as shown in FIG. 10 for RADA16 (SEQ ID NO:1), FIG. 11 for KLD12 (SEQ ID NO:2), and FIG. 12 for IEIK13 (SEQ ID NO:3).

Among other things, the present disclosure provides methodologies in accordance with which one or more certain peptide compositions are subjected to high shear stress so that one or more of their rheological properties is adjusted (e.g., viscosity is decreased) to an appropriate level so that the composition(s) become amenable to filtration, and in some embodiments to sterilizing filtration, and the composition(s) are subjected to such filtration, within a time period after the subjecting to shear stress selected so that filtration occurs while the rheological properties remain adjusted (e.g., before significant or complete restoration of such propert(ies) has occurred).

In general, as described herein, shear stress may be applied by application of a peptide composition to (and/or passage of a peptide composition through) a shear-thinning unit. In some embodiments, a shear-thinning unit is or comprises a needle, a membrane, and/or a screen. In some embodiments, a plurality of individual shear-thinning units is utilized, for example so that high-throughput filtration can be achieved.

In some embodiments, the present invention provides devices and methodologies that can achieve filtration of peptide compositions on a commercial scale.

Needle as a Shear-Thinning Unit

In some non-limiting embodiments, shear stress may be applied by injection through one or more needles. Thus, in some embodiments, one or more needles may be used as a shear-thinning unit.

In some embodiments, a needle may be at least about 1 mm long. In some embodiments, a needle may be at least about 2 mm long. In some embodiments, a needle may be at least about 5 mm long. In some embodiments, a needle may be at least about a 10 mm long. In some embodiments, a needle may be at least about 15 mm long. In some embodiments, a needle may be at least about 20 mm long. In some embodiments, a needle may be at least about 30 mm long. In some embodiments, a needle may be at least about 40 mm long. In some embodiments, a needle may be at least about 50 mm long.

In some embodiments, a needle may have a gauge within a range of about 20 to about 34. In some embodiments, a needle may have a gauge within a range of about 25 to about 34. In some embodiments, a needle may have a gauge of about 27 to about 34.

Figure 5:
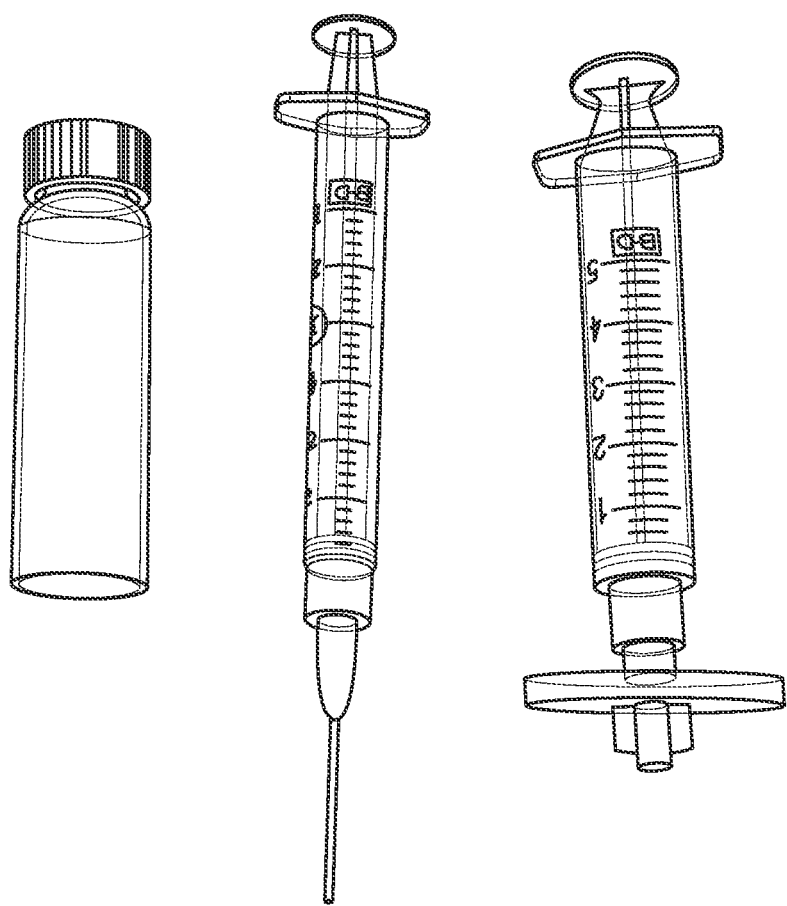
FIG. 5 provides a picture of peptides and devices needed for filtering viscous peptide solutions, for example, RADA16 (SEQ ID NO:1), KLD12 (SEQ ID NO:2), and IEIK13 (SEQ ID NO:3). Shear stress was applied through 30-gauge needle to peptide solutions (middle), so that the peptide solutions were filtered (right).

FIG. 5 discloses one non-limiting embodiment of a sterilization device in accordance with one or more non-limiting embodiments. As depicted, peptide composition (e.g., viscous solution of a self-assembling peptide) (left) may be transferred to the first syringe with a needle, injected to the second syringe (right), and then filtered.

Membrane as a Shear-Thinning Unit

Figure 13:
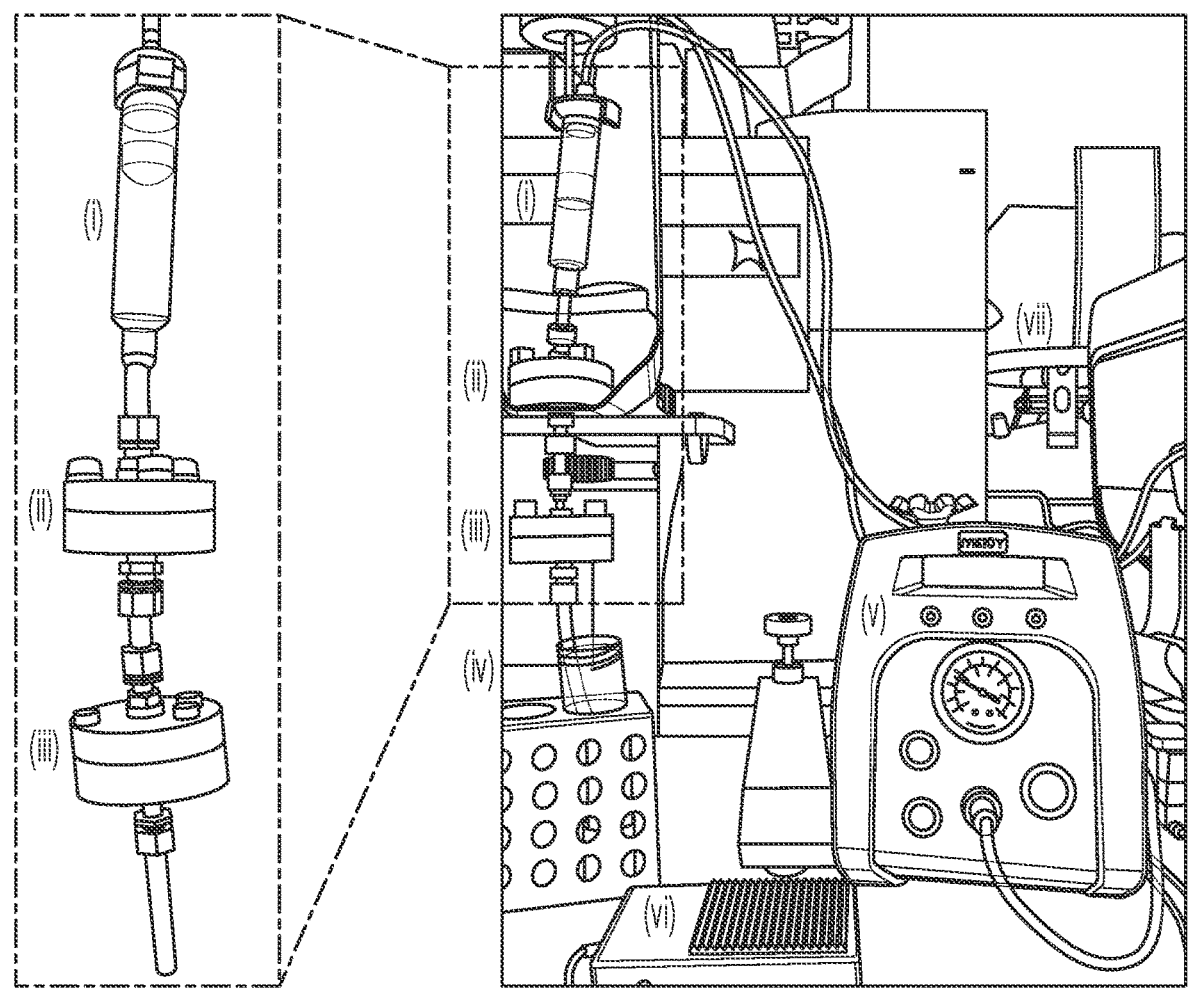
FIG. 13 shows exemplary devices for filtering viscous peptide solutions, for example, RADA16 (SEQ ID NO:1), KLD12 (SEQ ID NO:2), and IEIK13 (SEQ ID NO:3). Shear stress was applied through a shear-thinning unit with multiple pores. Peptide solution was dispensed with a syringe on the top (i). Peptide solution passed through the first shear-thinning chamber (25 mm filter holder, Millipore (ii)) where a shear-thinning unit with pores or holes was inserted to reduce the viscosity of peptide solution temporarily. Peptide solution then passed into second filtering chamber (25 mm filter holder, Millipore (iii)) where a filtering membrane was inserted to sterilize peptide solutions or remove particulates from peptide solutions. Filtered solution was received in a bottle (iv) for output. A high pressure dispenser was connected to the dispensing syringe (v). High pressure nitrogen gas was connected to the high pressure dispenser (vii).

In some embodiments, a shear-thinning unit utilized to apply shear stress to a peptide composition as described herein may be a device or entity characterized by micro- or nano-pores. FIG. 13 depicts one non-limiting embodiment of a sterilization device in accordance with one or more non-limiting embodiments of the present invention. As depicted, a peptide solution (e.g., a viscous solution of a self-assembling peptide) may be transferred to a dispensing syringe (or a pressure vessel), delivered to a first chamber with pores for shear stress, and then filtered in the second chamber. As will be understood by those skilled in the art, diameter size of membrane may vary depending on the amount of peptide solution.

In some embodiments, pore size of a shear-thinning unit may be about 0.45 µm to 120 µm. In some embodiments, pore size of a shear-thinning unit may be about 1 µm to 100 µm. In some embodiments, pore size of a shear-thinning unit may be about 3 µm to 80 µm. In some embodiments, pore size of a shear-thinning unit may be about 4 µm to 50 µm.

Screen as a Shear-Thinning Unit

In some embodiments, a shear-thinning unit may have micro- or nano-holes. In some embodiments, holes may be patterned or drilled on a plate whose thickness may be about 10 µm to 10 mm in some embodiments. FIG. 15 depicts one non-limiting embodiment of a sterilization device in accordance with one or more non-limiting embodiments of the present disclosure. A shear-thinning unit may be inserted into the first filtering chamber shown FIG. 13.

In some embodiments, holes in an embodiment of a shear-thinning unit described herein may have a largest dimension within the range of about may be about 0.5 µm to 200 µm. In some embodiments, such dimension may be within the range of about 0.5 µm to 100 µm. In some embodiments, such dimension may be within the range of about 0.5 µm to 80 µm. In some embodiments, such dimension may be within the range of about 0.5 µm to 50 µm.

In some embodiments, a shear-thinning unit of this embodiment may have a pitch between holes within the range of about 5 µm to about 10 mm.

In some embodiments, shear-thinning unit may be made, in whole or in part, of a material selected from the group consisting of stainless-steel, tungsten, titanium, similar metal, silicon, ceramic or plastic materials, and combinations thereof.

Applications

In some embodiments, peptide compositions to which technologies described herein are applied are then utilized in one or more applications that involve biological cells, tissues, or organisms (e.g., so that sterilized compositions are of particular utility).

As is known in the art, certain peptide compositions (e.g., certain compositions of self-assembling peptides) have proven to be particularly useful as matrices for cell growth in vivo and/or in vitro, and/or as void fillers, hemostats, barriers to liquid movement, wound healing agents, etc. In some embodiments, such compositions form peptide hydrogels with one or more desirable characteristics (e.g., pore and/or channel size, strength, deformability, reversibility of gel formation, transparency, etc).

Those skilled in the art, reading the present disclosure, will immediately appreciate its usefulness in a variety of contexts in which such peptide compositions, including gel compositions and especially including reversibly gelling compositions, are employed. Of particular interest are in vivo applications (e.g., surgical applications or other applications, particularly that permit or benefit from delivery via a cannula-type device, such as a needle, through which composition may be administered or applied).

EXEMPLIFICATION

Example 1: Filtration of High Viscous Peptide Solutions

The present Example describes, among other things, rheological properties of various peptide compositions (i.e., specifically of compositions of self-assembling peptides), and demonstrates significant variability of parameters such as viscosity, storage modulus (e.g., stiffness), loss modulus, and yield stress for different peptides and/or for different concentrations of the same peptide. The Example also demonstrates that certain of these solutions are not readily amenable to filtration. In particular, the Example demonstrates that high viscosity solutions of such peptides present challenges for filtration technologies. Rheological properties were determined for a variety of peptide solutions. Specifically, solutions of RADA16 (SEQ ID NO:1), IEIK13 (SEQ ID NO:3), and KLD12 (SEQ ID NO:2) per prepared at concentrations indicated below in Table 1. As can be seen, in general, higher concentration solutions showed higher max viscosity. Furthermore, peptides of different sequence showed different max viscosities in solutions of the same concentration. For example 2% KLD12 (SEQ ID NO:2), 2.5% KLD12 (SEQ ID NO:2), and 1.5% IEIK13 (SEQ ID NO:3) solutions have 2, 3.4, and 3.2 times higher maximum viscosities than 2.5% RADA16 (SEQ ID NO:1), respectively.

TABLE 1

Rheological properties of peptide solutions at selected concentrations

| Peptides | Conc. (%) | Storage Modulus (G')* (Pa) | Loss Modulus (G")* (Pa) | Yield Stress (Pa)*, # | Max. Viscosity (max η') (Pa · s)*, # |
|---|---|---|---|---|---|
| RADA16 | 1 | 74 | 12 | 15.9 | 2.3 |
| (SEQ ID | 1.5 | 158 | 30 | 20.0 | 3.4 |
| NO: 1) | 2 | 217 | 39 | 31.6 | 4.0 |
|  | 2.5 | 352 | 53 | 50.1 | 5.6 |
| IEIK13 | 1 | 719 | 77 | 39.8 | 12.9 |
| (SEQ ID | 1.5 | 1092 | 94 | 50.1 | 18.0 |
| NO: 3) | 2 | 1708 | 138 | — | — |
|  | 2.5 | 2213 | 174 | 100 | 40.2 |
| KLD12 | 1 | 140 | 25 | 25.1 | 2.0 |
| (SEQ ID | 1.5 | 292 | 46 | 39.8 | 7.1 |
| NO: 2) | 2 | 573 | 63 | 79.4 | 11.0 |
|  | 2.5 | 846 | 93 | 100 | 19.0 |

*at 1 Pa of oscillation stress
Maximum viscosity data was adapted in viscosity plots at the range of measured stress.

Each of the peptide solutions listed in Table 1 was subjected to filtration through a 0.2 Nalgene syringe filter with 25 mm cellulose acetate membranes. The 1% and 1.5% KLD12 (SEQ ID NO:2) solutions (which, as can be seen, are characterized by relatively low concentration, viscosity and/or stiffness) passed successfully through the filter. By contrast, the 2% and 2.5% KLD12 (SEQ ID NO:2) solutions and 1.5% IEIK13 (SEQ ID NO:3) solutions (which, as can be seen, are characterized by relatively high concentration, viscosity and/or stiffness) could not be passed successfully through the filter; instead, the filter burst.

Example 2: Autoclave Treatment of Peptide Solutions

The present Example demonstrates that some peptide compositions (i.e., specifically compositions of self-assembling peptides as described herein) are surprisingly stable to heat treatment. In particular, this Example demonstrates that certain peptide compositions maintain a stable molar mass even upon application of autoclave treatment at 121° C. for 25 minutes. The present Example therefore establishes that such compositions can successfully be sterilized through application of high heat (e.g., autoclave) technologies. The Example simultaneously demonstrates, however, that certain peptide compositions are not stable to such treatment.

Figure 1B:
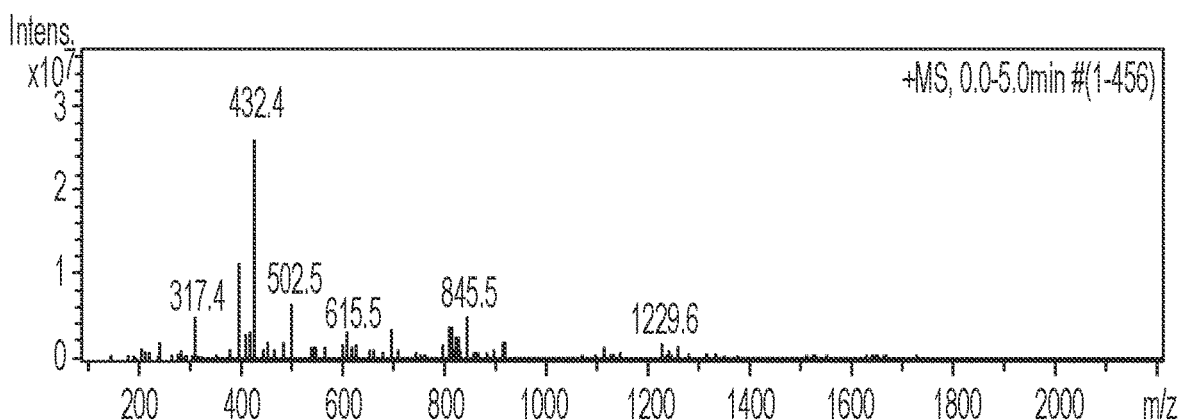
Figure 1C:
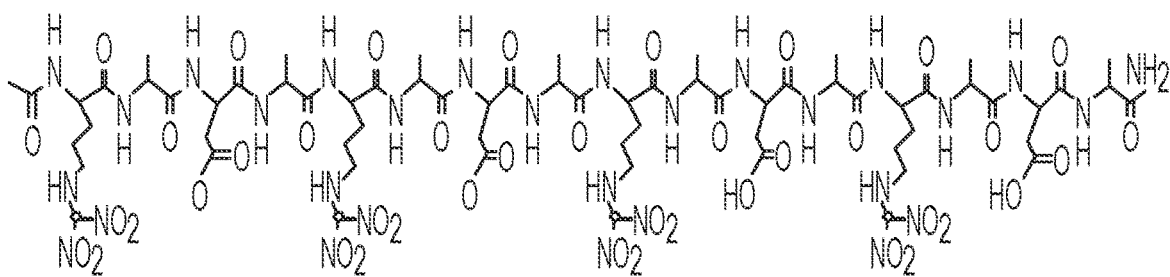
FIG. 1C illustrates exemplary RADA16 (SEQ ID NO:1) molecular structure; in the particular peptide composition that was analyzed, the protein was composed of RADARADARADARADA where the N-terminus and C-terminus are protected by acetyl and amino groups.
Figure 2A:
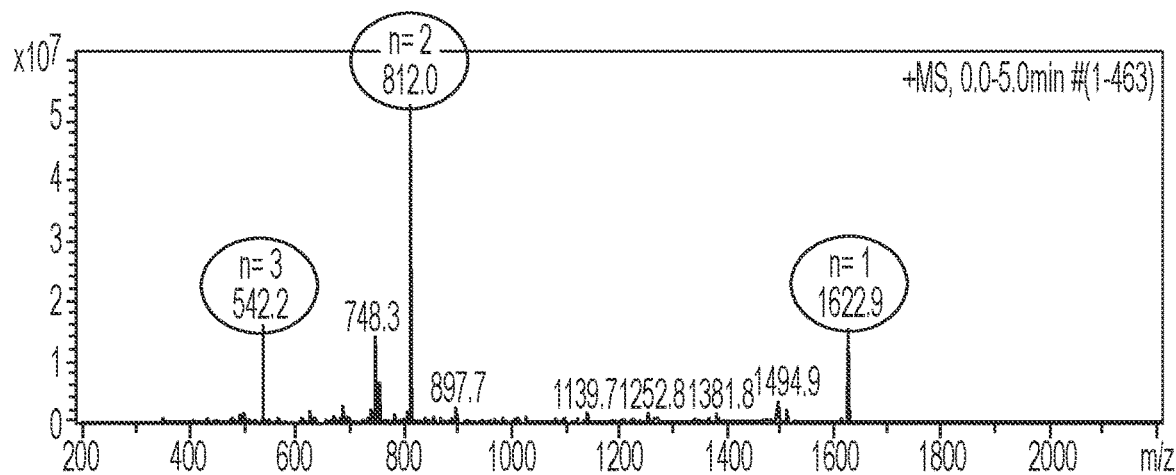
FIGS. 2A and 2B show exemplary mass spectrometry analysis of IEIK13 (SEQ ID NO:3) before and after autoclave treatment, to assess.
Figure 2B:
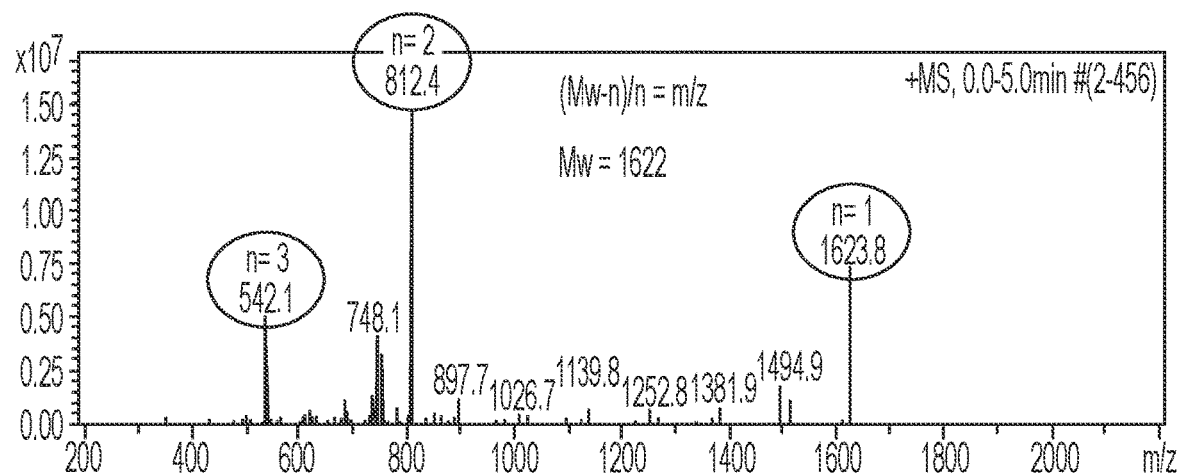
Figure 2C:
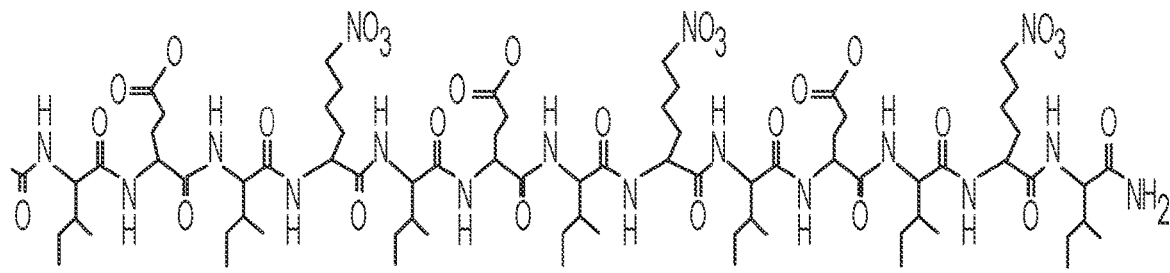
FIG. 2C illustrates exemplary IEIK13 (SEQ ID NO:3) molecular structure; in the particular peptide composition that was analyzed, the protein was composed of IEIKIEIK-IEIKI, where the N-terminus and C-terminus are protected by acetyl and amino groups.
Figure 3A:
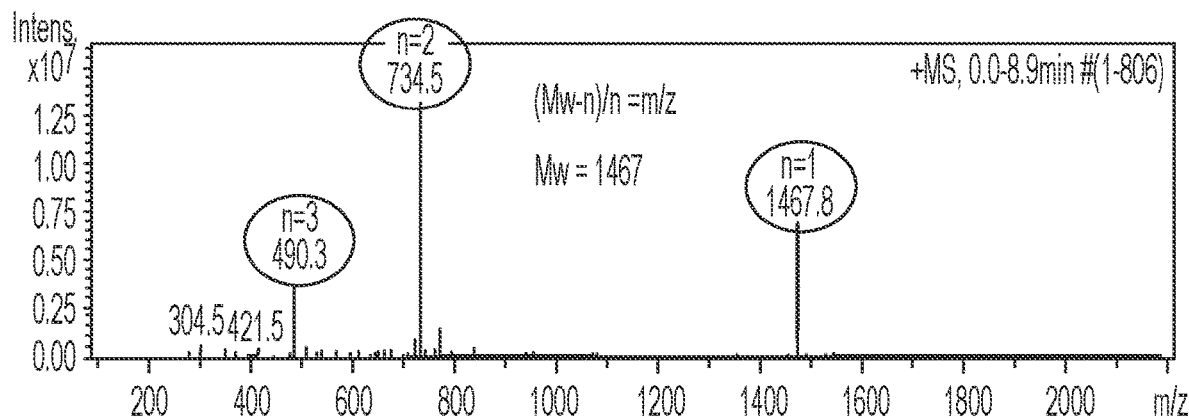
FIGS. 3A and 3B show exemplary mass spectrometry of KLD12 (SEQ ID NO:2) before and after autoclave treatment, to assess heat sensitivity.
Figure 3B:
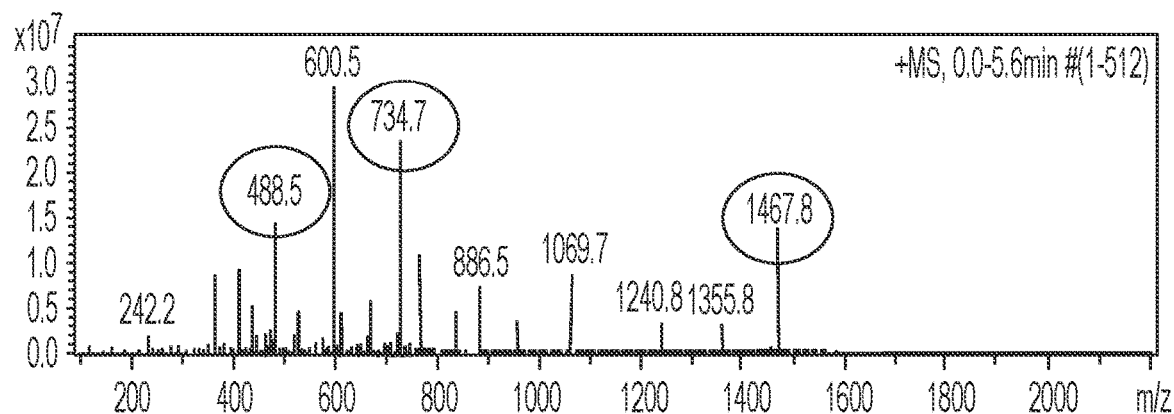
Figure 3C:
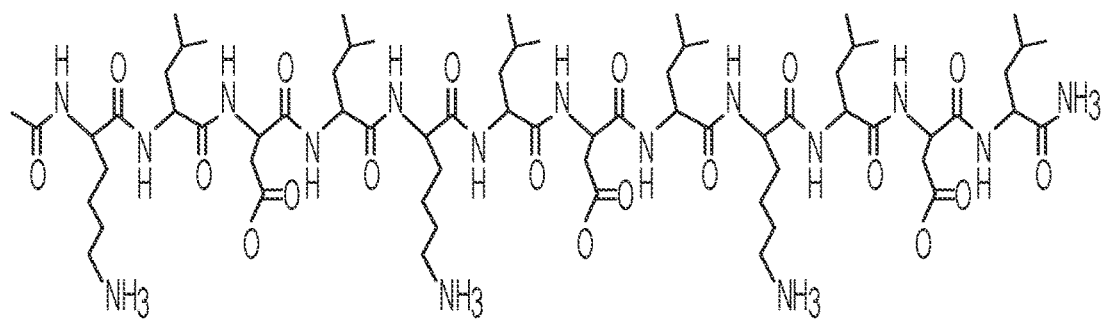
FIG. 3C illustrates exemplary KLD12 (SEQ ID NO:2) molecular structure; in the particular peptide composition that was analyzed, the protein was composed of KLDLKLDKKLDL, where the N-terminus and C-terminus are protected by acetyl and amino groups.

FIGS. 1-3 present results of autoclave treatment for certain compositions of RADA16 (SEQ ID NO:1), IEIK13 (SEQ ID NO:3), and KLD12 (SEQ ID NO:2), respectively.

The measured molar mass of RADA16 (SEQ ID NO:1), prior to autoclave treatment, was 1712, which matches its calculated molar mass. However, the mass spec analysis demonstrated that RADA16 (SEQ ID NO:1) was degraded during the autoclave treatment, thereby demonstrating that this technique cannot be used for sterilization of such a RADA16 (SEQ ID NO:1) composition.

The measured molar mass of IEIK13 (SEQ ID NO:3), prior to autoclave treatment, was 1622, which also matches its calculated molar mass. Mass spec analysis demonstrated that IEIK13 (SEQ ID NO:3) was not degraded after the autoclave treatment, thereby demonstrating that this technique can usefully be employed for sterilization of such an IEIK13 (SEQ ID NO:3) composition.

The measured molar mass of KLD12 (SEQ ID NO:2), prior to autoclave treatment, is 1467, which matches its calculated molar mass. KLD12 (SEQ ID NO:2) was partially degraded during autoclave treatment. As KLD12 (SEQ ID NO:2) was degraded during autoclave treatment, it was determined that autoclave treatment is not a preferred technique for sterilization of such KLD12 (SEQ ID NO:2) compositions; a conventional filtration approach to sterilization was carried out on KLD12 (SEQ ID NO:2) at several concentrations of peptide.

Figure 4:
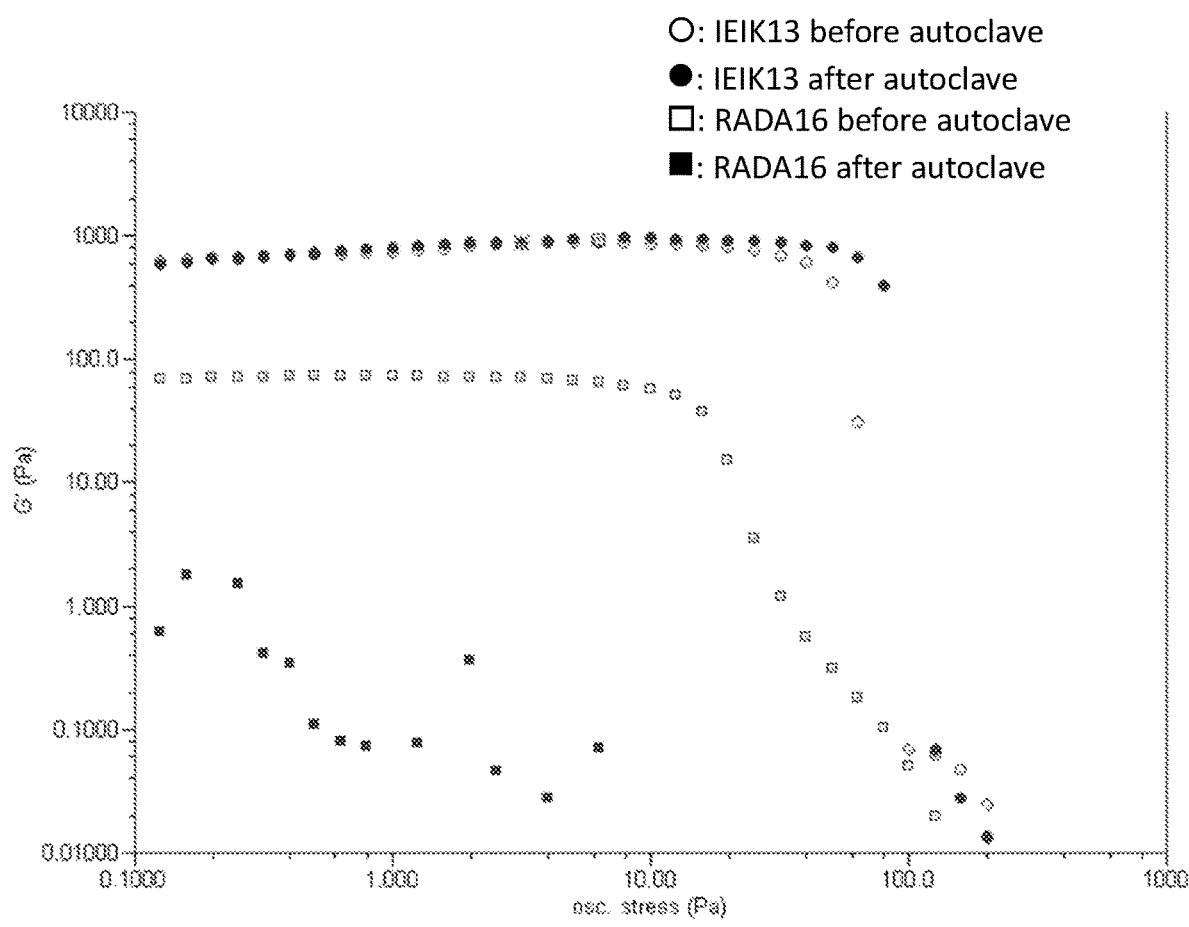
FIG. 4 shows exemplary time sweep tests of RADA16 (SEQ ID NO:1) and IEIK13 (SEQ ID NO:3) before and after autoclave treatment.

Rheological properties of certain peptide compositions were determined before and after autoclaving. The data are shown in FIG. 4. As can be seen, autoclaved IEIK13 (SEQ ID NO:3) surprisingly exhibited almost identical rheological strength as non-autoclaved IEIK13 (SEQ ID NO:3), while RADA16 (SEQ ID NO:1) displayed a dramatic decrease of rheological strength.

Autoclave treatment may be used for sterilization of IEIK13 (SEQ ID NO:3) compositions as described herein, but should be avoided for RADA16 (SEQ ID NO:1) compositions.

Example 3: Rheological Properties of Peptide Compositions with Application of Shear Stress The present Example demonstrates that applied shear stress may decrease viscosity and/or stiffness of certain peptide solutions, and furthermore demonstrates that such decrease in viscosity and/or stiffness can render the compositions amenable to various and/or processing technologies (e.g., filtration) to which the compositions are not amenable absent such treatment.

Shear Flow Test

Figure 9:
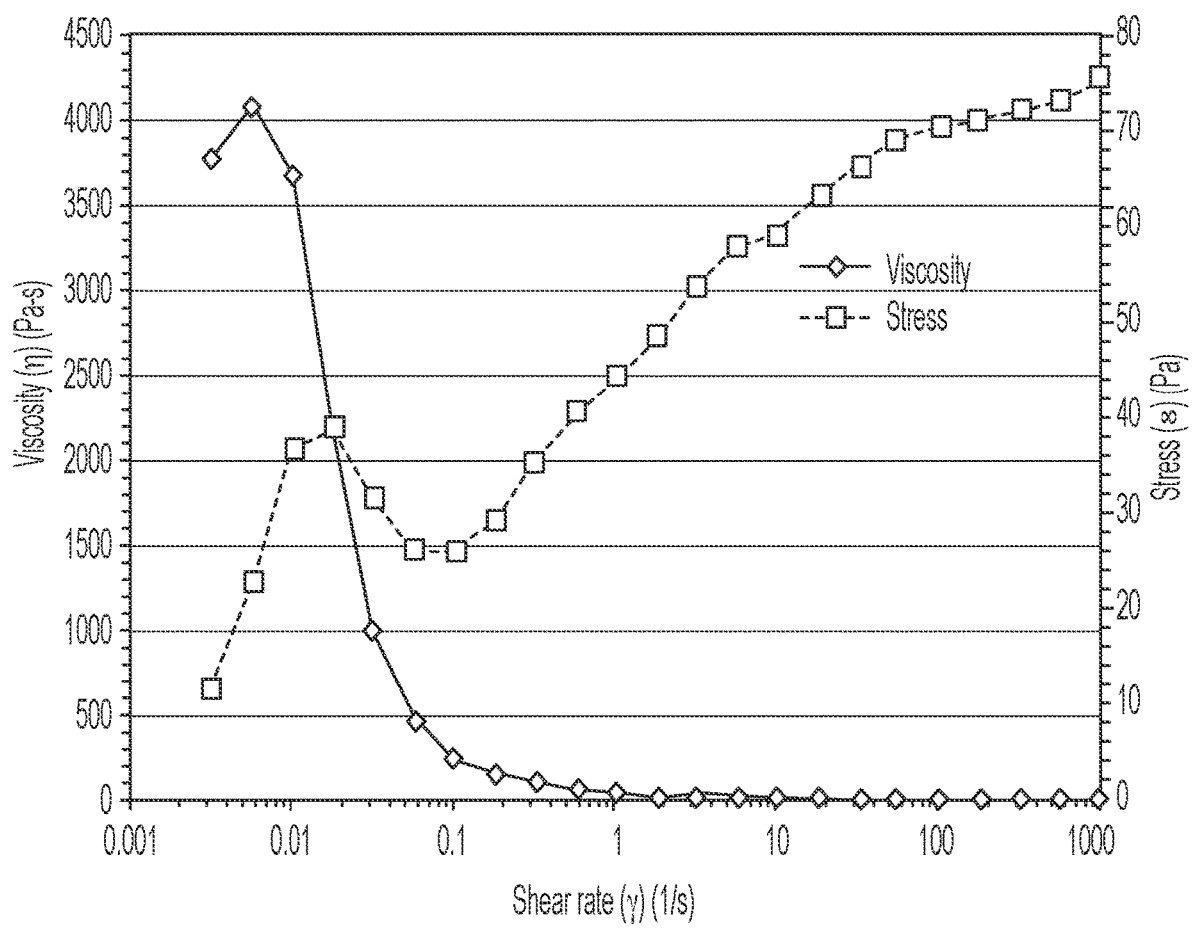
FIG. 9 shows an exemplary flow viscosity test performed from 0.003 to 1000 1/sec of shear rate on 2.5% RADA16 (SEQ ID NO:1) solution.

Shear flow tests were performed on peptide solutions using a rheometer (DHR-1, TA Instruments) with 20 mm plates. Results are shown in FIG. 9 for 2.5% RADA16 (SEQ ID NO:1) solutions and FIG. 10 for 1.5% IEIK13 (SEQ ID NO:3) solutions. As can be seen, both 2.5% RADA16 (SEQ ID NO:1) and IEIK13 (SEQ ID NO:3) 1.5% solutions showed a typical shear thinning properties. That is, as shear rate increased, their viscosities were dramatically dropped. As shear rate increased, shear stress immediately increased, and then slightly decreased when viscosity reached a plateau. The yield stress was about 40 Pa for 2.5% RADA16 (SEQ ID NO:1) solution and about 60 Pa for 1.5% IEIK13 (SEQ ID NO:3) solution.

Viscosity Recovery

Figure 11:
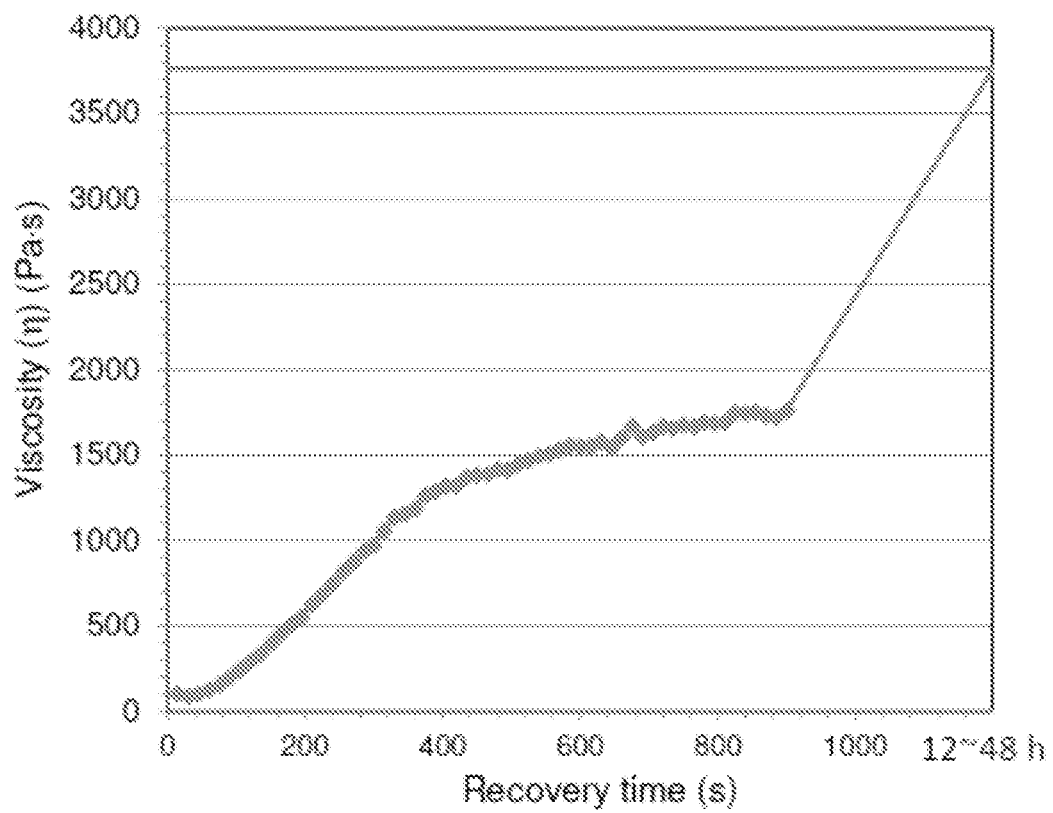
FIG. 11 shows exemplary viscosity measurements of 2.5% RADA16 (SEQ ID NO:1) as a function of time to demonstrate viscosity recovery. At time=0, shear stress was applied to the peptides, so that the viscosity was reduced. The horizontal line indicates the original viscosity of 2.5% RADA16 (SEQ ID NO:1).
Figure 12:
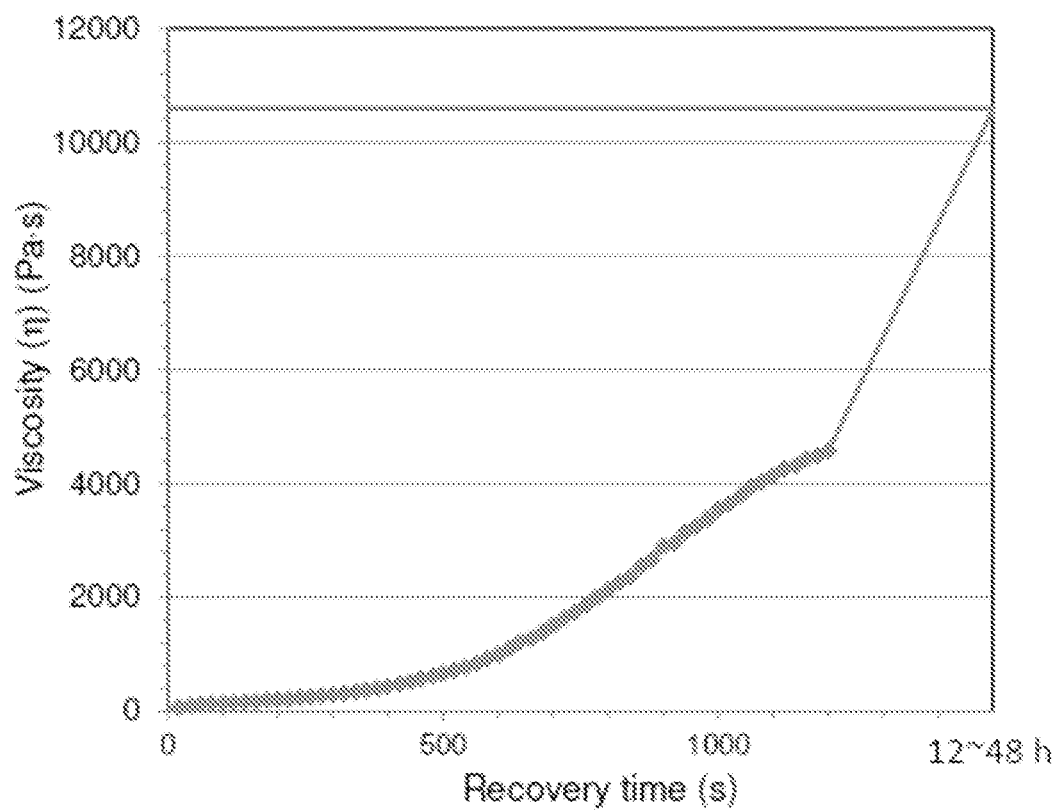
FIG. 12 shows exemplary viscosity measurements of 1.5% IEIK13 (SEQ ID NO:3) as a function of time to demonstrate viscosity recovery. At time=0, shear stress was applied to the peptides, so that the viscosity was reduced. The horizontal line indicates the original viscosity of 1.5% IEIK13 (SEQ ID NO:3).

The viscosity recovery times of RADA16 (SEQ ID NO:1) and IEIK13 (SEQ ID NO:3) solutions were evaluated after application of high shear stress. Using a DHR-1 rheometer (TA Instruments), viscosity changes of 2.5% RADA16 (SEQ ID NO:1) and 1.5% IEIK13 (SEQ ID NO:3) solutions were measured with flow tests at 0.005 l/sec of shear rate after applying 1000 l/sec of shear rate to samples for 1 min. RADA16 (SEQ ID NO:1) and IEIK13 (SEQ ID NO:3) solutions showed a typical thixotropic behavior, which means their viscosity were slowly recovered. Without wishing to be bound by any particular theory, we propose that rheological property recovery times for these solutions may be based on re-assembly of peptide molecules into structures (e.g., nano-fibers) in the solutions. Complete reassembling times of 2.5% RADA16 (SEQ ID NO:1) and 1.5% IEIK13 (SEQ ID NO:3) solution were about 12 to 48 hours. The results are shown in FIG. 11 for 2.5% RADA16 (SEQ ID NO:1) solution and FIG. 12 for 1.5% IEIK13 (SEQ ID NO:3) solution.

Storage Modulus Recovery

The percentages of recovery back to the original storage modulus at 1 min and 20 min after injection peptide compositions through a 30 gauge needle are listed in Table 2. The recovery rate of IEIK13 (specifically, of a 2.5% IEIK13 solution; SEQ ID NO:3) was the fastest among the peptide solutions, showing 100% recovery to the original storage modulus in 20 min. KLD12 (SEQ ID NO:2) was the slowest among those tested to recover; it showed only 23% recovery to the original storage modulus in 20 min (for 2.5%). In some non-limiting embodiments, it may take about 12 to 48 hours for full recovery to an original modulus after passage through a needle (e.g., injection).

TABLE 2

Recovery to the original storage modulus at 1 min and 20 min after injection through 30-gauge needle

| | | 1% | | | 2.5% | | |
|---|---|---|---|---|---|---|---|
| | | Before injection | 1 min after injection | 20 min after injection | Before injection | 1 min after injection | 20 min after injection |
| RADA16 (SEQ ID | Storage modulus( Pa) | 74 Pa | 6.8 Pa | 40 Pa | 352 Pa | 67 Pa | 196 Pa |

TABLE 2-continued

Recovery to the original storage modulus at 1 min and 20 min after injection through 30-gauge needle

| | | 1% | | | 2.5% | | |
|---|---|---|---|---|---|---|---|
| | | Before injection | 1 min after injection | 20 min after injection | Before injection | 1 min after injection | 20 min after injection |
| NO: 1) | Recovery % to the original modulus | — | 9.2% | 54% | — | 19% | 56% |
| KLD12 (SEQ ID NO: 2) | Storage modulus (Pa) | 140 Pa | 0.68 Pa | 59 Pa | 846 Pa | 57 Pa | 196 Pa |
| | Recovery % to the original modulus | — | 0.5% | 42% | — | 6.7% | 23% |
| IEIK13 (SEQ ID NO: 3) | Storage modulus (Pa) | — | — | — | 2213 Pa | 632 Pa | 2248 Pa |
| | Recovery % to the original modulus | — | — | — | — | 29% | 100% |

Figure 6:
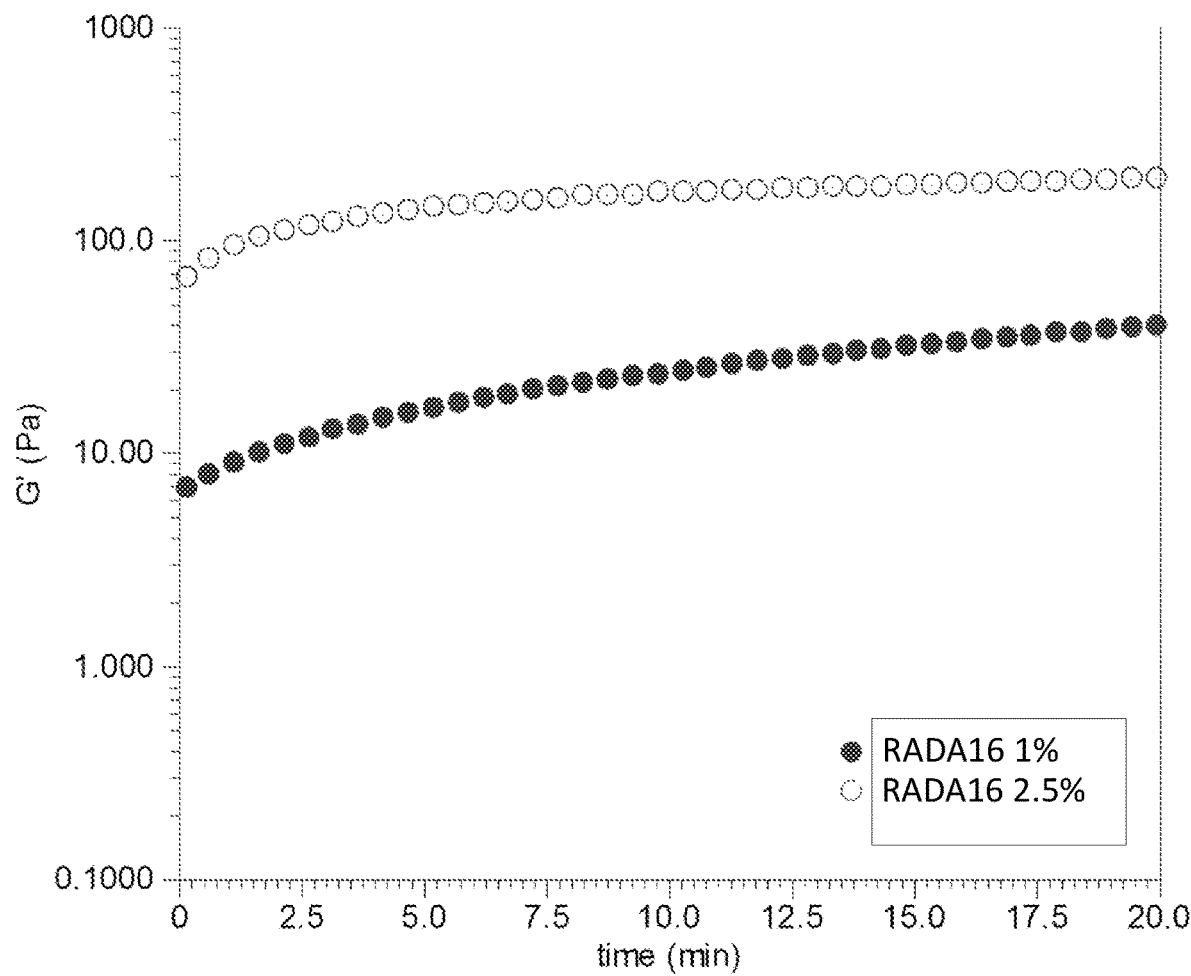
FIG. 6 shows exemplary time sweep tests of 1% and 2.5% RADA16 (SEQ ID NO:1) performed at 1 Pa and 10 rad/s. RADA16 (SEQ ID NO:1) was injected through 30-gauge needle so that applied shear stress reduced stiffness of the peptides. The measurements were started 1 minute after the injection.
Figure 7:
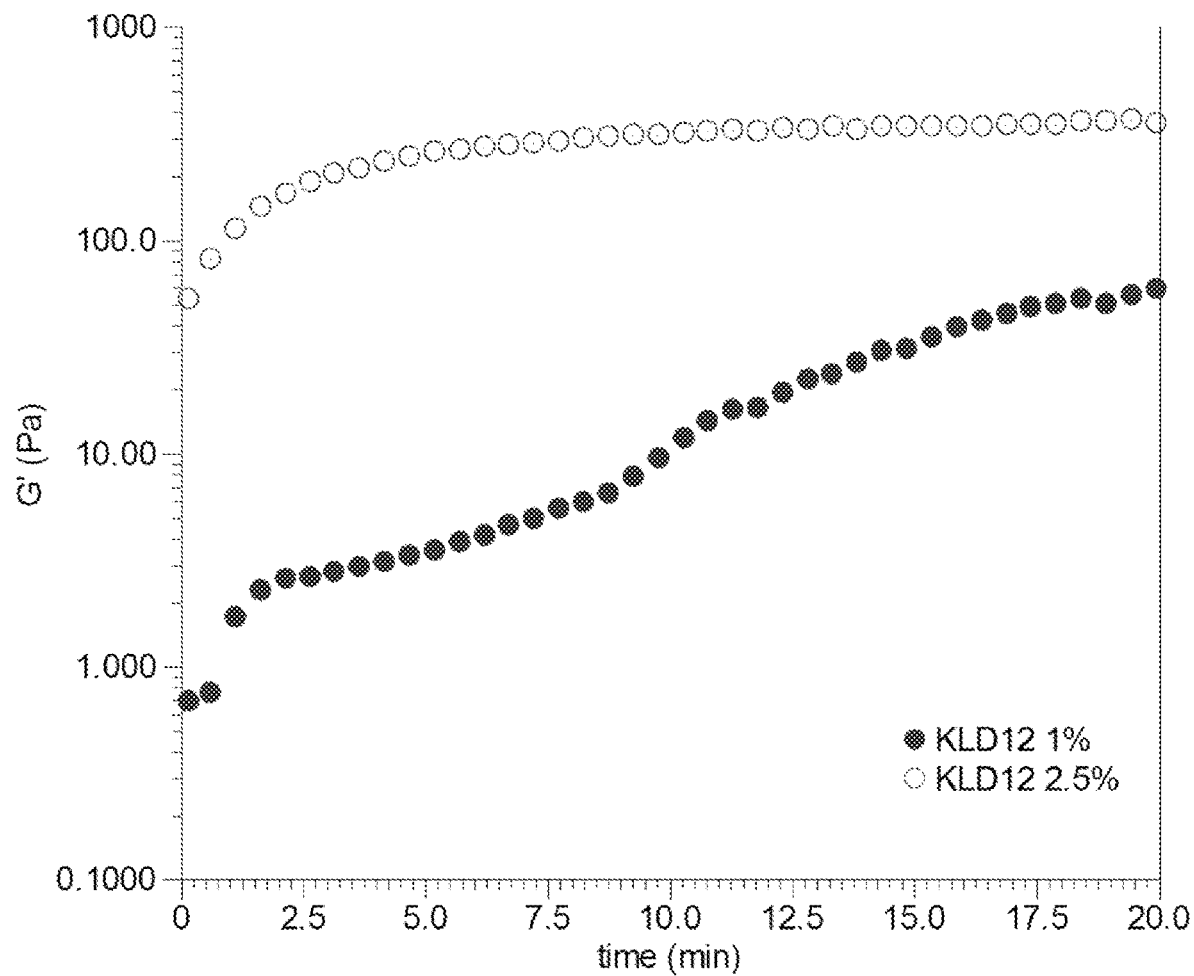
FIG. 7 shows exemplary time sweep tests 1% and 2.5% KLD12 (SEQ ID NO:2) performed at 1 Pa and 10 rad/s. KLD12 (SEQ ID NO:2) was injected through 30-gauge needle so that the applied shear stress reduced stiffness of the peptides. The measurements were started 1 minute after the injection.
Figure 8:
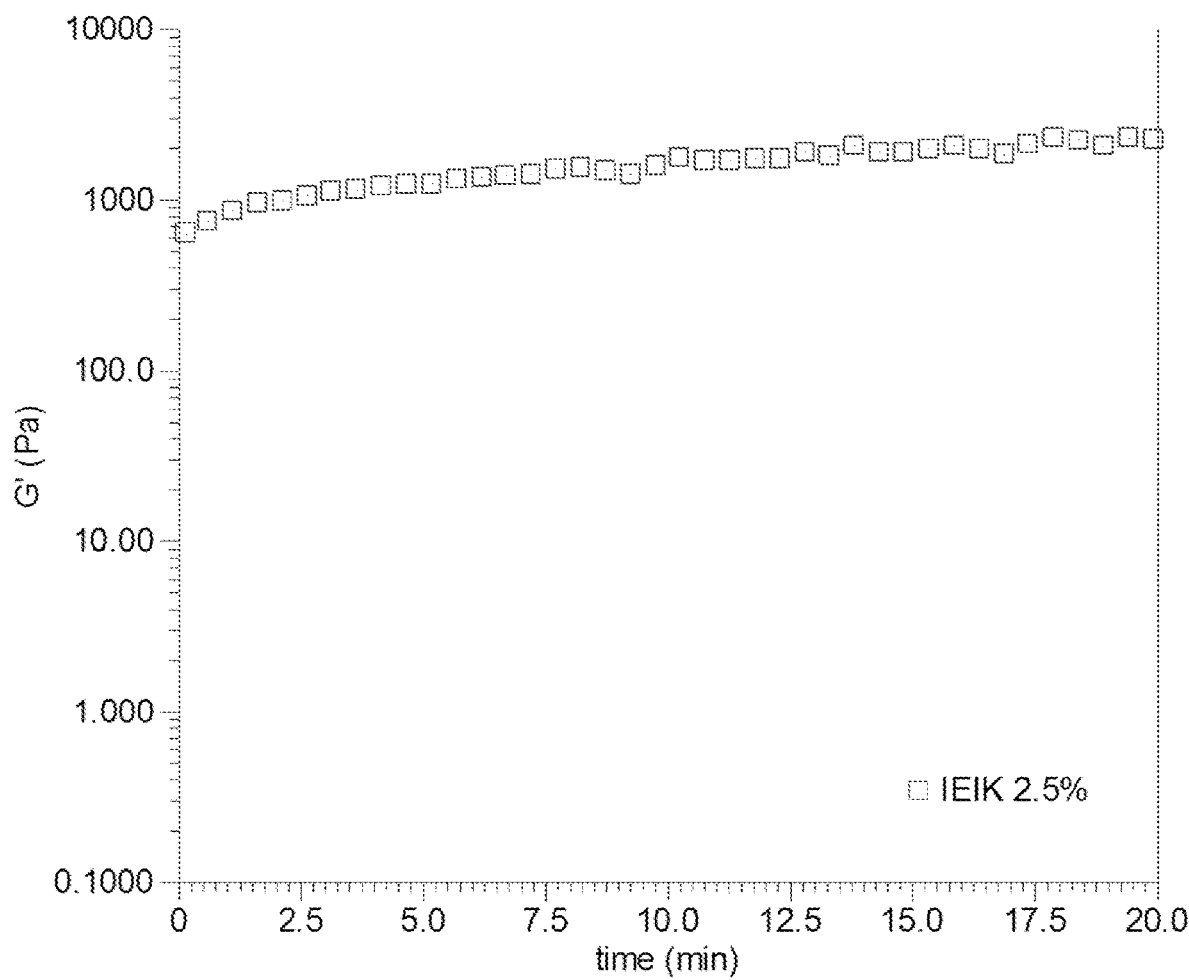
FIG. 8 shows exemplary time sweep tests 2.5% IEIK13 (SEQ ID NO:3) performed at 1 Pa and 10 rad/s. IEIK13 (SEQ ID NO:3) was injected through 30-gauge needle so that the applied shear stress reduced stiffness of the peptides. The measurements were started 1 minute after the injection.

Rheological measurements were performed for RADA16 (SEQ ID NO:1) and IEIK13 (SEQ ID NO:3) solutions after injecting them through 30 gauge needles. The results showed a logarithmic increase of storage modulus from 1 minute after injection. The results are shown in FIG. 6 for RADA16 (SEQ ID NO:1), FIG. 7 for KLD12 (SEQ ID NO:2), and FIG. 8 for IEIK13 (SEQ ID NO:3).

Example 4: A Needle as a Shear-Thinning Unit

The present Example describes a filtration process for peptide compositions (specifically, of self-assembling peptides as described herein) using a needle as a shear-thinning unit. In particular, the present Example demonstrates that application of appropriate shear stress (e.g., via passage through a shear-thinning unit) can alter rheological properties of the composition (e.g., can reduce viscosity and/or stiffness, etc.) so that it can successfully be passed through a filter such as, for example, a sterilizing filter).

FIG. 5 depicts one non-limiting embodiment of a sterilization device in accordance with the present disclosure. As depicted, the device includes a first syringe that applies sheer stress to the composition sufficient to alter its rheological properties such that it successfully passes through a second syringe that is fitted with a membrane filter of appropriate pore size to achieve sterilization of the composition. Specifically, the depicted device includes a first syringe with a 30 gauge needle (0.3 mm×25 mm, Endo irrigation needle with double side vent, Transcodent, Germany) (middle) and a second syringe with a membrane filter (right). A viscous 2.5% KLD12 (SEQ ID NO:2) solution (left) was transferred to the first syringe, and was then injected into the second syringe (right) and then filtered through the membrane filter. Using this method, 2.5% KLD12 (SEQ ID NO:2) solutions were successfully filtered.

Example 5: High Throughput Shear-Thinning Unit

The present Example describes certain shear thinning units. The principle of operation is like that for the first needle described above. Specifically, each shear-thinning unit applies shear stress appropriate and sufficient to adjust one or more rheological properties of an applied peptide composition so that the composition becomes amenable to filtration, and specifically to filtration through a sterilizing filter. In some embodiments, multiple needles or equivalents may be used as a shear-thinning unit.

Membrane Filter

This Examples demonstrates use of a with membrane filter (pore size>0.45 μm) as a shear-thinning unit. Viscous 2.5% KLD12 (SEQ ID NO:2) or 1.5% IEIK13 (SEQ ID NO:3) solutions may be transferred to a dispensing syringe (or a pressure vessel), delivered to a first chamber with a shear-thinning unit (for example, pore size ranging from 0.45 μm to 120 μm), and then filtered through a filtering membrane (for example, pore size: 0.2 μm) in the second chamber.

Figure 14:
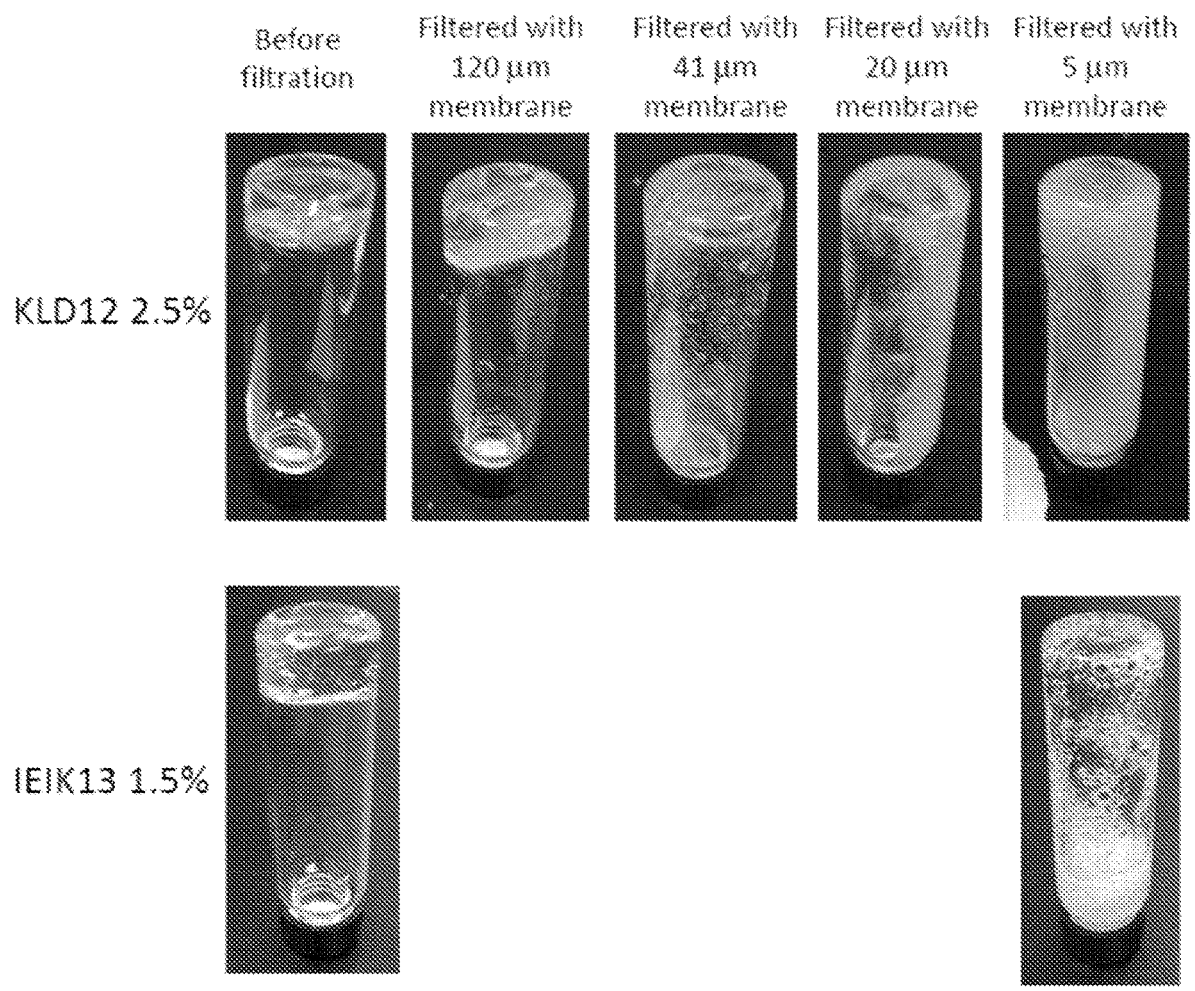
FIG. 14 shows visual observation of viscosity after applying shear stress to 2.5% KLD12 (SEQ ID NO:2) solution and 1.5% IEIK13 (SEQ ID NO:3) solution. The top row includes pictures of 2.5% KLD12 (SEQ ID NO:2). The bottom row includes pictures of 1.5% IEIK13 (SEQ ID NO:3). The solutions in the most left column stay on the top of the vials. The solutions in the most right column (after applying shear stress) have low viscosity, so that most materials are located at the bottom of vials.
Figure 15A:
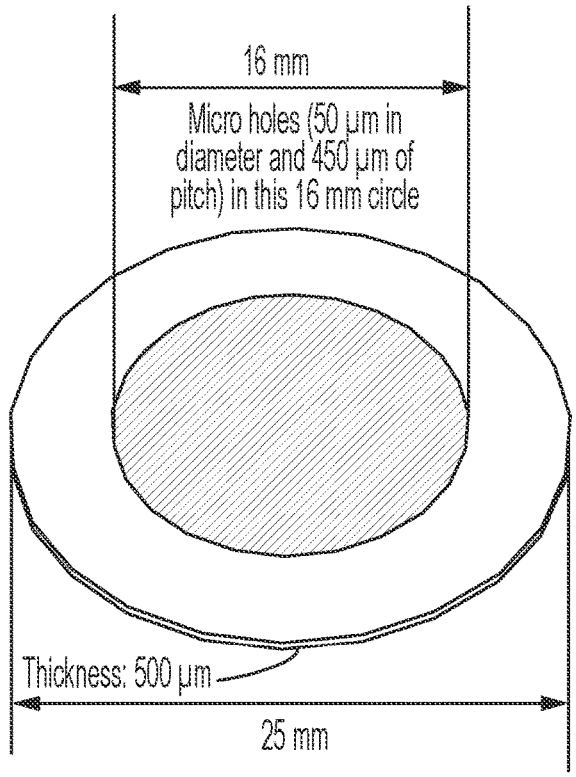
FIGS. 15A, 15B, 15C, and 15D show materials and devices (a micro- or nano-hole screen) for filtering viscous peptide solutions such as RADA16 (SEQ ID NO:1), KLD12 (SEQ ID NO:2), and IEIK13 (SEQ ID NO:3).
Figure 15B:
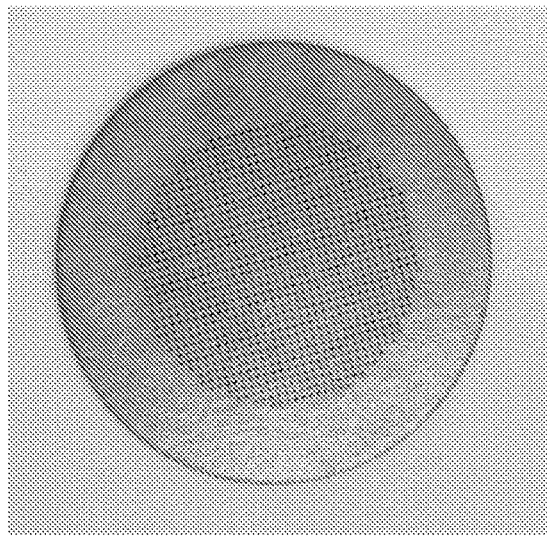
Figure 15C:
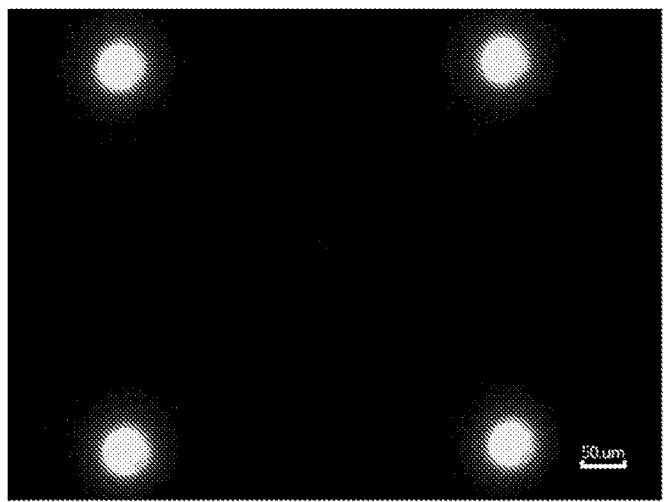
Figure 15D:
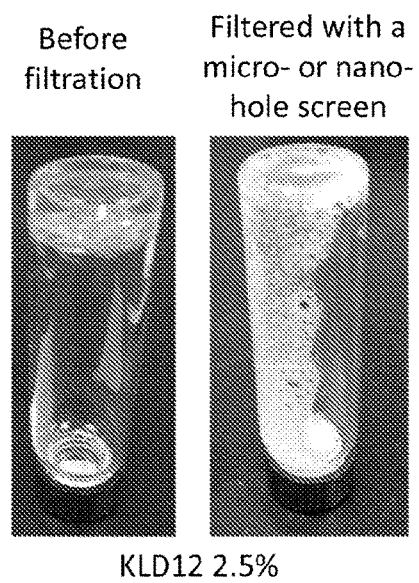

To examine the effect of pore size in the shear-thinning unit on viscosity change of viscous peptide solutions, 2.5% KLD12 (SEQ ID NO:2) and 1.5% IEIK13 (SEQ ID NO:3) solutions were passed through selected pore sizes, and their apparent viscosity changes were evaluated. 2.5% KLD12 (SEQ ID NO:2) solutions passed through the shear-thinning unit with the pore sizes of 41 μm, 20 μm, and 5 μm. Viscosity of the solutions was decreased enough to flow down when a vessel containing it was flipped over. Though 2.5% KLD12 (SEQ ID NO:2) solutions that had passed through the shear-thinning unit with the pore size of 120 μm were slightly less viscous than pre-passage 2.5% KLD12 (SEQ ID NO:2) compositions, they remained too viscous to flow down in the container-inversion test. The viscosity of 1.5% IEIK13 (SEQ ID NO:3) solutions was reduced significantly when passed through a membrane with a pore size of 5 μm. Results are shown in FIG. 14.

1.0% RADA16 (SEQ ID NO:1) solutions were studied for viscosity reduction with a shear-thinning unit (shown in FIG. 13). 1.0% RADA16 (SEQ ID NO:1) solution, which shows shear thinning and thixotropic behavior, was passed through a shear-thinning unit at 50 psi of injection pressure. The solution showed 1.4~1.7 mL/min of output. The solution could not be passed through a filter (0.2 μm pore size) at 50 psi of injection pressure (i.e., without prior exposure to a shear-thinning unit). However, water, which is a representative Newtonian fluid, showed that output flow rate was relatively consistent. The results are shown in Table 3.

TABLE 3

Filtering abilities of the system shown in FIG. 13 for RADA16 (SEQ ID NO: 1) 1% solution and water.

| Materials | Output through filter: 0.2 μm pore size* | Output through shear-thinning unit (41 μm pore size) + filter (0.2 μm pore size)* | Output through shear-thinning unit (20 μm pore size) + filter (0.2 μm pore size)* | Output through shear-thinning unit (5 μm pore size) + filter (0.2 μm pore size)* |
|---|---|---|---|---|
| Water (at 25 psi) | 42 mL/min | 35 mL/min | 41 mL/min | 33 mL/min |
| RADA16 (SEQ ID NO: 1) 1.0% (at 50 psi) | 0 mL/min | 1.4 mL/min | 1.7 mL/min | 1.6 mL/min |

*Diameters of shear-thinning units and filter are 25 mm.

As demonstrated above, 2.5% KLD12 (SEQ ID NO:2 and 1.5% IEK13 (SEQ ID NO:3 solutions were not able to be filtered through a 0.2 μm Nalgene syringe filter with 25 mm cellulose acetate membranes. 2.5% RADA16 (SEQ ID NO:1) is not usually amenable to filtration through 0.2 μm membrane. 2.5% RADA16 (SEQ ID NO:1), 1.5% IEIK13 (SEQ ID NO:3), and 2.5% KLD12 (SEQ ID NO:2) solutions were able to be filtered after being exposed to a shear-thinning unit at 100 psi of injection pressure showing 3.8, 12.5, and 11.4 mL/min of output, respectively. The solutions were not able to be filtered without the shear-thinning unit. A shear-thinning unit shown in FIG. 16 may be successfully utilized for sterilization and filtration of viscous peptide solutions which are not easily filtered. The results are shown in Table 4.

TABLE 4

Filtering abilities filtering system shown in FIG. 13 for 2.5% RADA16 (SEQ ID NO: 1), 1.5% IEIK13 (SEQ ID NO: 3), 2.5% KLD12 (SEQ ID NO: 2) solutions.

| | Output through filter (0.2μ pore size) at 100 psi.* | Output through shear-thinning unit (5 μm pore size) + filter (0.2 μm pore size) at 100 psi.* |
|---|---|---|
| RADA16 (SEQ ID NO: 1) 2.5% | 0 mL/min | 3.8 mL/min |
| IEIK13 (SEQ ID NO: 3) 1.5% | 0 mL/min | 12.5 mL/min |
| KLD12 (SEQ ID NO: 2) 2.5% | 0 mL/min | 11.4 mL/min |

*Diameters of membranes are 25 mm.

Screen

This Examples are demonstrates successful use of a screen with micro- and/or nano-holes as a shear-thinning unit. Viscous 2.5% KLD12 (SEQ ID NO:2) or 1.5% IEIK13 (SEQ ID NO:3) solutions may be transferred to a dispensing syringe (or chamber), injected to a first chamber that includes a shear-thinning unit with micro- and/or nano-holes, and then filtered through the membrane filter (pore size: 0.2 μm) in the second chamber. Instead of syringe for injection, a high pressure chamber may be used to deliver a peptide composition. Membrane size (e.g., diameter) and/or other characteristics (e.g., pore size, etc) may be selected to accommodate amount of peptide composition to be passed through it.

TABLE 5

Filtering abilities of the micro-hole screen system shown in FIG. 13 and FIG. 15 for 2.5% RADA16 (SEQ ID NO: 1), 1.5% IEIK13 (SEQ ID NO: 3), 2.5% KLD12 (SEQ ID NO: 2) solutions.

| | Output through filter (0.2μ pore size) at 100 psi.* | Output through shear-thinning unit (screen with micro holes[#]) + filter (0.2 μm pore size) at 100 psi.* |
|---|---|---|
| RADA16 (SEQ ID NO: 1) 2.5% | 0 mL/min | 4.2 mL/min |
| IEIK13 (SEQ ID NO: 3) 1.5% | 0 mL/min | 5.0 mL/min |
| KLD12 (SEQ ID NO: 2) 2.5% | 0 mL/min | 11.5 ml/min |

*Diameters of membranes are 25 mm.
[#]hole size is 50 μm in diameter, pitch of holes is 450 μm, and depth of holes is 500 μm.

What is claimed is:

1. A method for sterilizing a liquid peptide composition, wherein the peptide in the liquid peptide composition comprises IEIK13 as set forth in SEQ ID NO:3, and wherein the peptide is N-terminal acetylated and/or C-terminal amidated, the method comprising subjecting the liquid peptide composition to heat treatment performed at about 121° C. for about 25 minutes.

2. The method of claim 1, wherein the method does not involve sterilizing filtration.

3. The method of claim 1, wherein the liquid peptide composition has a peptide concentration within the range of about 0.01% and about 10%.

4. The method of claim 1, wherein the method does not degrade the peptide.

5. A method for sterilizing a liquid peptide composition, wherein the peptide in the liquid peptide composition comprises IEIK13 as set forth on SEQ ID NO:3, and wherein the peptide is N-terminal acetylated and/or C-terminal amidated, the method comprising subjecting the liquid peptide composition to autoclave treatment.

6. The method of claim 5, wherein the method does not involve sterilizing filtration.

7. The method of claim 5, wherein the liquid peptide composition has a peptide concentration within the range of about 0.01% and about 10%.

8. The method of claim 5, wherein the method does not degrade the peptide.

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: synthetic

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 12
<212> TYPE: PRT
```

```
<213> ORGANISM: Artificial Sequence
<220> FEATURE:
<223> OTHER INFORMATION: synthetic

<400> SEQUENCE: 2

Lys Leu Asp Leu Lys Leu Asp Leu Lys Leu Asp Leu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Ile Glu Ile Lys Ile Glu Ile Lys Ile Glu Ile Lys Ile
1               5                   10

<210> SEQ ID NO 4
<211> LENGTH: 4
<212> TYPE: PRT
<213> ORGANISM: Artificial Sequence
<220> FEATURE:
<223> OTHER INFORMATION: synthetic

<400> SEQUENCE: 4

Arg Ala Asp Ala
1

<210> SEQ ID NO 5
<211> LENGTH: 4
<212> TYPE: PRT
<213> ORGANISM: Artificial Sequence
<220> FEATURE:
<223> OTHER INFORMATION: synthetic

<400> SEQUENCE: 5

Lys Leu Asp Leu
1

<210> SEQ ID NO 6
<211> LENGTH: 4
<212> TYPE: PRT
<213> ORGANISM: Artificial Sequence
<220> FEATURE:
<223> OTHER INFORMATION: synthetic

<400> SEQUENCE: 6

Ile Glu Ile Lys
1
```